US008734339B2

(12) United States Patent
Rao et al.

(10) Patent No.: US 8,734,339 B2
(45) Date of Patent: May 27, 2014

(54) ELECTRONIC SKIN PATCH FOR REAL TIME MONITORING OF CARDIAC ACTIVITY AND PERSONAL HEALTH MANAGEMENT

(75) Inventors: Raman K. Rao, Palo Alto, CA (US); Sunil K. Rao, Palo Alto, CA (US); Rekha K. Rao, Palo Alto, CA (US); Sanjay K. Rao, Palo Alto, CA (US)

(73) Assignee: IP Holdings, Inc., Palo Alto, CA (US)

( * ) Notice: Subject to any disclaimer, the term of this patent is extended or adjusted under 35 U.S.C. 154(b) by 0 days.

(21) Appl. No.: 11/001,668

(22) Filed: Nov. 30, 2004

(65) Prior Publication Data

US 2012/0191147 A1 Jul. 26, 2012

(51) Int. Cl.
*A61B 5/00* (2006.01)
*A61B 5/024* (2006.01)
*A61B 5/0205* (2006.01)
*G06F 19/00* (2011.01)

(52) U.S. Cl.
CPC ............... *A61B 5/00* (2013.01); *A61B 5/0002* (2013.01); *A61B 5/0006* (2013.01); *A61B 5/02438* (2013.01); *A61B 5/0205* (2013.01); *A61B 5/4836* (2013.01); *A61B 5/6801* (2013.01); *G06F 19/30* (2013.01); *G06F 19/322* (2013.01); *G06F 19/323* (2013.01); *G06F 19/3481* (2013.01); *Y10S 128/92* (2013.01)
USPC ............ 600/300; 607/3; 607/7; 705/2; 705/3; 702/188; 128/920; 600/372; 600/391; 600/509

(58) Field of Classification Search
USPC ................... 600/300, 301; 128/903–905, 920
See application file for complete search history.

(56) References Cited

U.S. PATENT DOCUMENTS

| 4,465,401 A | 8/1984 | Stoddord et al. |
| 4,675,401 A | 6/1987 | Robin |
| 4,675,653 A | 6/1987 | Priestly |
| 5,195,130 A | 3/1993 | Weiss et al. |
| 5,242,382 A | 9/1993 | Gorsuch et al. |
| 5,379,341 A | 1/1995 | Wan |
| 5,410,738 A | 4/1995 | Diepstraten et al. |
| 5,465,401 A | 11/1995 | Thompson |
| 5,513,242 A | 4/1996 | Mukerjee et al. |

(Continued)

FOREIGN PATENT DOCUMENTS

WO WO 92/03884 3/1992

OTHER PUBLICATIONS

U.S. Appl. No. 09/680,611, filed Oct. 6. 2000 in the name of Rao et al., Non-final Office Action mailed Aug. 8, 2002.

(Continued)

*Primary Examiner* — Bill Thomson
*Assistant Examiner* — Marie Archer
(74) *Attorney, Agent, or Firm* — Levine Bagade Han LLP

(57) ABSTRACT

A novel wearable electronic skin patch sensor device configured for the real time acquisition, processing and communicating of cardiac activity and other types of biological information within a wired or wireless network is disclosed. A system level scheme for networking the sensor device with client devices that include intelligent personal health management appliances, cellular telephones, PDAs, portable computers, personal computers, RFID Tags and servers is disclosed. The sensor device and the system enable distributed processing, archival and correlation of the biological information with biometrics, gastronomic information, user profiles and health factors that include height, weight, blood pressure and physical activity facilitating real time personal health management at any time and any place.

50 Claims, 10 Drawing Sheets

(56) References Cited

U.S. PATENT DOCUMENTS

| | | | |
|---|---|---|---|
| 5,517,553 | A | 5/1996 | Sato |
| 5,539,391 | A | 7/1996 | Yuen |
| 5,551,953 | A | 9/1996 | Lattin et al. |
| 5,555,258 | A | 9/1996 | Snelling et al. |
| 5,559,794 | A | 9/1996 | Willis et al. |
| D374,675 | S | 10/1996 | Sakai et al. |
| 5,565,929 | A | 10/1996 | Tanaka |
| 5,566,205 | A | 10/1996 | Delfine |
| 5,577,118 | A | 11/1996 | Sasaki et al. |
| 5,672,154 | A | 9/1997 | Sillen et al. |
| 5,741,317 | A | 4/1998 | Ostrow |
| 5,845,263 | A | 12/1998 | Camaisa et al. |
| 5,860,957 | A | 1/1999 | Jacobsen et al. |
| 5,862,803 | A * | 1/1999 | Besson et al. .................. 600/508 |
| 5,980,934 | A | 11/1999 | Reber et al. |
| 6,175,752 | B1 * | 1/2001 | Say et al. ...................... 600/345 |
| 6,219,638 | B1 | 4/2001 | Padamanabahan et al. |
| 6,314,405 | B1 | 11/2001 | Richardson |
| 6,425,524 | B2 | 7/2002 | Pentel |
| 6,527,712 | B1 | 3/2003 | Brown et al. |
| 6,553,244 | B2 | 4/2003 | Lesho et al. |
| 6,579,231 | B1 | 6/2003 | Phipps |
| 6,629,776 | B2 * | 10/2003 | Bell et al. ...................... 374/170 |
| 6,771,995 | B2 | 8/2004 | Kurnik et al. |
| 6,814,706 | B2 * | 11/2004 | Barton et al. .................. 600/549 |
| 6,865,261 | B1 | 3/2005 | Rao et al. |
| 7,009,511 | B2 | 3/2006 | Mazar et al. |
| 2002/0019584 | A1 | 2/2002 | Schulze et al. |
| 2002/0126036 | A1 | 9/2002 | Flaherty et al. |
| 2002/0147135 | A1 | 10/2002 | Schnell |
| 2003/0149343 | A1 | 8/2003 | Siegel et al. |
| 2003/0208113 | A1 | 11/2003 | Mault et al. |
| 2004/0003256 | A1 | 1/2004 | Coffy et al. |
| 2004/0102931 | A1 * | 5/2004 | Ellis et al. ...................... 702/188 |
| 2004/0176674 | A1 * | 9/2004 | Nazeri ............................ 600/382 |
| 2005/0003470 | A1 | 1/2005 | Nelson et al. |
| 2005/0010087 | A1 | 1/2005 | Banet et al. |
| 2005/0076909 | A1 * | 4/2005 | Stahmann et al. ....... 128/204.23 |
| 2005/0080322 | A1 * | 4/2005 | Korman ........................ 600/300 |
| 2005/0182389 | A1 | 8/2005 | LaPorte et al. |
| 2005/0192557 | A1 | 9/2005 | Brauker et al. |
| 2005/0197554 | A1 | 9/2005 | Polcha |
| 2005/0251424 | A1 * | 11/2005 | Sanders et al. ..................... 705/3 |
| 2005/0277872 | A1 | 12/2005 | Colby, Jr. et al. |
| 2006/0004263 | A1 * | 1/2006 | Feliss et al. .................. 600/300 |
| 2006/0004271 | A1 | 1/2006 | Peyser et al. |
| 2006/0036134 | A1 | 2/2006 | Tarassenko et al. |
| 2008/0046038 | A1 | 2/2008 | Hill et al. |
| 2008/0139907 | A1 | 6/2008 | Rao et al. |
| 2008/0191866 | A1 | 8/2008 | Falck et al. |

OTHER PUBLICATIONS

U.S. Appl. No. 09/680,611, filed Oct. 6, 2000 in the name of Rao et al., Final Office Action mailed Apr. 22, 2003.
U.S. Appl. No. 09/680,611, filed Oct. 6, 2000 in the name of Rao et al., Non-final Office Action mailed Jan. 15, 2004.
U.S. Appl. No. 09/680,611, filed Oct. 6, 2000 in the name of Rao et al., Notice of Allowance mailed Sep. 23, 2004.
U.S. Appl. No. 09/680,611, filed Oct. 6, 2000 in the name of Rao et al., Notice of Allowance mailed Feb. 4, 2005.
U.S. Appl. No. 11/708,282, filed Feb. 20, 2007 in the name of Rao et al., Non-final Office Action mailed Jul. 1, 2010.
U.S. Appl. No. 11/708,282, filed Feb. 20, 2007 in the name of Rao et al., Final Office Action mailed Feb. 28, 2011.
U.S. Appl. No. 11/708,395, filed Feb. 20, 2007 in the name of Rao et al., Non-final Office Action mailed Sep. 18, 2009.
U.S. Appl. No. 11/708,395, filed Feb. 20, 2007, in the name of Rao, Final Office Action mailed Jun. 18, 2010.
U.S. Appl. No. 11/018,862, filed Dec. 19, 2004, in the name of Rao, Non-Final Office Action mailed Jun. 9, 2010.
U.S. Appl. No. 11/018,862, filed Dec. 19, 2004, in the name of Rao, Final Office Action mailed Oct. 13, 2010.
U.S. Appl. No. 11/018,862, filed Dec. 19, 2004, in the name of Rao, Non-final Office Action mailed Apr. 19, 2011.
U.S. Appl. No. 11/708,269, filed Feb. 20, 2007, in the name of Rao et al., Non-final Office Action mailed Oct. 13, 2010.

* cited by examiner

ELECTRONIC SKIN PATCH FOR REAL TIME MONITORING OF CARDIAC ACTIVITY AND PERSONAL HEALTH MANAGEMENT

CROSS REFERENCE TO RELATED APPLICATIONS

Abbreviations:
Cellular Telephone is abbreviated as CT and Mobile Device is abbreviated as MD.
Intelligent Personal Health Management Appliance is abbreviated as IPHMA
Personal Health Management is abbreviated as PHM

BACKGROUND OF THE INVENTION

The objective of the present invention is teaching novel intelligent appliances for measuring and/or monitoring various human body functions/parameters such as body weight, body girth, body height, blood pressure and cardiac activity with the objective of further relating the acquired biological data with various other information including health and gastronomic information.

The prior art of record does not teach the means for real time acquisition of various biological data utilizing intelligent appliances and additionally does not teach the means for relating the acquired biological data for correlation to specific items of foods ingested and various activities expended, including physical exercise, for providing a means for an individual to pro actively manage his/her own health. The present invention teaches a novel method for real time personal health management of an individual by the individual him/her self or by the individual in conjunction with a health professional located locally or across the world such as on the Internet.

In order to get quality care from a health professional, significant and relevant information about the individual/patient must be provided to the health professional including the trends and history of various biological parameters. Often patients relate random information and subjective opinions about the human condition without providing objective data and data trends. Consequently, the un-structured and non quantified information provided by the patient severely limits the ability of the health professional to diagnose a health problem and further limits the ability of the patient to get quality care in real time.

Therefore, there is a need for a new class of intelligent appliances, referred in here as intelligent personal health management appliances that enable the individual to personally acquire one or more types of biological information in real time, archive said information for co-relation with factors such as diet and other activities including physical exercise, for personal health management by the individual him/her self or for personal health management in conjunction with a qualified health professional. The cost of quality health care is increasing much faster than inflation in most countries and it is becoming beyond the reach of a large segment of the world population. The ability to get access in real time to trained health professionals and the amount of time that the health professional spends in examining the patient is woefully in adequate. Additionally, patients in certain geographical areas do not have access to urgent care or to experts that have the requisite training related to a specific problem. However, the potential for wired broadband connectivity or wireless connectivity in most areas of the world is realizable faster than the potential for the deployment of qualified health professionals in non urban areas.

The present invention teaches novel methods and novel appliances for real time data acquisition of biological information, for archiving said data for contemporaneous utility or for utility at a selected time, for analyzing said data, for determining trends, for communication of said data to one or more health professionals and for comprehensive real time management of the personal health of an individual in a cost effective manner in accordance with the quality/cost objectives acceptable to the individual.

SUMMARY OF THE INVENTION

The old adage, " You are what you eat", has increasing relevance today as significant generalized correlations about the health of human beings in relation to the ingestion of certain foods, medications and other material such as alcohol, tobacco and non prescription drugs is being published and continually updated by affirmation and or negation of the results. However, this information is often confusing and conflicting and does not provide a clear cut means for personal utility to an individual. In addition, there is a need for modifying the old adage to a new adage, "You are what you eat, how you behave and how you act", since a significant body of evidence suggests that medications, smoking, prescription/non prescription drugs, physical activities, occupational activities, environmental factors, stress and other high risk behavior often have a correlation to the physical and mental health of an individual. The problem that urgently needs a solution is, how does an individual take charge of his/her own personal health? How does an individual get real time data about him/her self? How can the personal data be compared for relevance to group data for a similar problem? How can the personal data be tracked in real time and over a short/long period of time for trends? And how can the individual make personal health management decisions by him/her self or in conjunction with the best experts available locally or globally by leveraging the communication capabilities of intelligent appliances?

The present invention teaches novel methods and appliances to solve these problems not addressed in the prior art. A new class of intelligent personal health management appliances, hereafter referred to as intelligent IPHM appliances, wherein in personal health management is abbreviated as PHM, is disclosed. Various other important objectives of the present invention are also enumerated below. Other objectives may become apparent to those knowledgeable in the art and the invention is not to be construed as limited to the specific objectives enumerated herein:

A. System Level Scheme for Networking Intelligent Personal Health Management Appliances:

1. An objective of the present invention is an intelligent networking scheme for connecting personal health management appliances by wired or wireless means with stationary devices, mobile devices, a local server, a central server and a network server for providing the capability for the individual to manage different aspects of the individual's personal health in the home environment, office environment, institutional environment or on the road including in a transportation environment.

2. An objective of the present invention is to identify an individual and an intelligent personal health management appliance by a plurality of means, including by a unique identification number, by an imbedded/external optically readable tag, by an external radio frequency enabled RF ID Tag, by an internal to the human body radio frequency enabled tag and other identification methods; and use said identification methods in a comprehensive manner in conjunction with an ubiquitous mobile devices such as cellular telephones, PDAs and other mobile devices for personal health monitoring and management.

3. Another objective is to uniquely identify the individual by speech/voice recognition, photo, finger print and other biometric identification methods to ensure that the health information acquired is uniquely and securely related to the specific individual in real time for accurate personal health management. The biometric and other personal information is secured and made available with permission levels set by the individual by means of a secure server such as an escrow server.

4. Another objective of the present invention is to enable the mobile devices such as cellular telephones, PDAs and other mobile devices to perform the additional functions of one or more selected personal health monitoring, health delivery and health management functions by having said measurement, monitoring and delivery capabilities built-in or by working in conjunction with other stationary/portable intelligent personal health management appliances.

5. An object of the invention is to utilize a mobile device such as a cellular telephone, PDA and other mobile devices configured with an intelligent keyboard system or similar capabilities to acquire various biometric information including a photo, finger print, voice print, retinal scan, handwriting recognition and other authentication methods used singly or in selected combinations to authenticate the individual user or other healthcare providers for operation in conjunction with an intelligent personal health management appliance. The biometric data and other health information are enabled for maintenance on a secure server such as an escrow server.

6. Another objective of the invention is to configure an intelligent personal health management appliance with an intelligent keyboard system or other similar implementations to authenticate the user(s) using one or more selected authentication schemes that include voice/speech recognition, hand writing recognition, photo recognition, finger print recognition, retinal scan recognition, associated RFID Tag recognition and associated mobile device recognition to enable the selected levels of authentication used singly or in combination; further ensuring that the secure user specific data bases are protected for authorized read/write and access by authorized individuals with permission levels set by the user.

7. Another objective is to use an RFID Tag associated with the intelligent personal health management appliance by itself or in conjunction with an RF ID Tag associated with the individual user, such that the information necessary to seamlessly operate the intelligent appliance for the specific benefit of one or more users is accomplished with the elimination of manual data entry resulting in the real time data being read from/written to various appliances, RF ID Tags, mobile devices, stationary devices and servers and their respective storage and databases by wired and or wireless means.

B. Intelligent Weight Measurement Appliances:

The present invention also teaches an intelligent appliance for measurement of human body weight in conjunction with related software resident within the intelligent weight measurement appliance itself, within a mobile device, within a stationary device, and within a server for real time personal health management.

8. An objective of the present invention is an intelligent appliance for the measurement and acquisition of human body weight in real time or at selected times with the ability to communicate by wired or wireless means the acquired data of human body weight and other parameters to a central server and or a mobile device.

9. Another objective of the present invention is for the intelligent weight measurement appliance to perform various selected functions in conjunction with the personal health management software resident within the intelligent weighing appliance itself or on a local, central and network server or a combination thereof, enabling the individual by him/her self or in conjunction with a selected health professional, to manage one or more aspects of the individual's personal health in a selected manner and at a selected time.

10. Another objective of the present invention is a method for relating human body weight of a specific individual to other information related to the specific individual, said information including gastronomic information such as the ingestion of various foods, medications and other items, and further including various activities such as physical exercise that the individual has engaged in.

C. Intelligent Appliances for Real Time Measurement of the Electrical Activity of the Heart and for Obtaining an ECG, Electro Cardiogram of Individuals:

11. An objective of the present invention is to enable a stationary/portable mobile intelligent personal health management appliance for electro cardio gram, ECG measurement wherein the measurement signals are acquired via leads and the user is identified with an associated RF ID Tag from which information is read including the ability to write ECG information to the RF ID Tag. The intelligent ECG appliance further has the ability to be networked with other servers/mobile devices/intelligent appliances and additionally enabling correlation of the ECG information with other information including gastronomic information.

12. An object of the invention is an intelligent ECG appliance as in objective 11 above except that in this case there are no wired leads and instead a series of wireless contacts are used to acquire and transmit the signals to the intelligent ECG appliance or other appliances/devices/servers.

13. An object of the invention is an intelligent ECG appliance as in objective 11 above except that in this case the mobile device such as a cellular telephone, PDA or other mobile devices acquire the signals for the ECG measurement through wired leads and either process the signals within the mobile device itself or in conjunction with a remote ECG appliance. The mobile device is enabled as simply a pass through device and or has the software and processing capability to provide an electro cardio gram in real time.

14. An object of the intelligent ECG appliance as in objective 13 above except that in this case wireless contacts are used to acquire the signals from the body in conjunction with a mobile device that is proximately located.

D. Intelligent Appliances for Real Time Measurement of the Electrical Activity of the Heart and for Delivering a Defibrillation Electrical Energy Pulse to Individuals:

15. An object of the invention is to enable delivery of defibrillation energy pulses to the heart in by wired or wireless contacts in conjunction with a mobile device that provides the electrical energy pulses.

E. Intelligent Appliances for Real Time Measurement of the Blood Pressure and Pulse Rate of Individuals:

Certain individuals are characterized by low blood pressure and others more commonly suffer from high blood pressure also known as hypertension. Blood pressure is also a function of various other factors such as anxiety, moods, depression and other factors. Blood pressure is generally controllable by moderating certain activities both physical and mental. More importantly blood pressure is controllable by moderating the ingestion of certain foods. As an example individuals with high blood pressure can control the condition by limiting the intake of salt, fatty foods, by exercise and by generally controlling the body weight. High blood pressure if untreated by proper diet, exercise and or medications may cause strokes that in some cases are fatal. There is a need for an intelligent appliance that provides the individual, the real time means for monitoring and controlling hypertension in conjunction with other factors such as the ingestion of different types of food.

16. An objective of the present invention is a wired/wireless blood pressure measurement appliance with the ability for the measurement of blood pressure levels at selected times/time intervals, the tracking of the measured data, the comparison of the measured data with prior history and the correlation of the blood pressure levels with different types of foods ingested and the activities. The blood pressure measurement appliance having the ability for making a measurement, for processing/storing of the software and information in the unit itself, in a server or a combination of the unit and the server.

17. Another objective of the present invention is the capability for configuring a mobile device such a cell phone, a PDA and other mobile devices for the additional functions of a blood pressure measurement, wherein the mobile device, including with appropriate attachments performs said functions in a standalone manner, with other attachments and or in conjunction with a local, central and network server. Additionally, having the ability to correlate the measured blood pressure levels with one or more other data such as the medications ingested, food ingested and different types of activities.

F. Intelligent Appliances for Real Time Measurement of Body Girth:

18. An objective of the present invention is an intelligent appliance for measuring the girth or circumference of the waist of a human body in real time, wherein the measured values are stored within the intelligent appliance or communicated to a mobile device, a server and other appliances 19. An objective of the present invention is to relate the measured girth values to gastronomic information, physical activity such as exercise, medications and other medical conditions G. Intelligent Appliances for Real Time Measurement of Body Height:

20. An objective of the present invention is an intelligent appliance for measuring the height of a human body accurately, wherein the measured values are stored within the intelligent appliance or communicated to a mobile device, a server and other appliances.

21. An objective of the present invention is to relate the measured height values to body mass index, gastronomic information, best diets for controlling the growth in height, optimal diets for controlling weight and other physical conditions for a given value of height, physical activity such as exercise, medications and other medical conditions.

Other objects, features and advantages of the present invention will become apparent from the following detailed description when taken in conjunction with the accompanying drawings.

BRIEF DESCRIPTION OF THE EMBODIMENTS OF THE INVENTION

The accompanying drawings, which are incorporated in and form a part of this specification, illustrate embodiments of the invention and, together with the description, serve to explain the principles of the invention:

FIG. 1 shows a system level scheme for networking of one or more intelligent appliances as represented in the prior disclosure by the common inventors, now U.S. Pat. Nos. 6,169,789 and 6,480,587.

FIG. 2 shows a system level architecture for wired or wireless networking of intelligent personal health management appliances, wherein the appliance is able to operate in a standalone manner or in conjunction with an RF ID Tag, a mobile device, a local server, a central server, an escrow server and a network server utilizing processing, storage, software and databases contained therein.

FIG. 3 shows a system level architecture for wired or wireless networking of an intelligent personal health management appliance for measuring and tracking the weight of humans, animals and various materials including edible and inedible materials. The appliance is able to operate in a standalone manner or in conjunction with an RF ID Tag, a mobile device, a local server, a central server and a network server utilizing processing, storage, software and databases contained there in.

FIG. 4 shows a system level architecture for wired or wireless networking of an intelligent personal health management appliance for an electro cardio gram, ECG, evaluation of the heart. The appliance is able to operate in a standalone manner or in conjunction with an RF ID Tag, a local server, a central server and a network server utilizing processing, storage, software and databases contained there in; the system herein using electrical wires/leads and paste on connectors for obtaining electrical signals through the skin.

FIG. 5 shows a system level architecture for wired or wireless networking of an intelligent personal health management appliance for an electrocardiogram evaluation of the heart. The appliance is able to operate in a standalone manner or in conjunction with an RF ID Tag, a local server, a central server and a network server utilizing processing, storage, software and databases contained there in; the system herein using paste on wireless connectors with the ability to transmit the acquired electrical signals remotely via a transmitter attached to each connector.

FIG. 6 shows a system level architecture for wired or wireless networking of an intelligent personal health management appliance for an electrocardiogram evaluation of the heart. The appliance is able to operate in a standalone manner or in conjunction with an RF ID Tag, a local server, a central server and a network server utilizing processing, storage, software and databases contained there in; the system herein using electrical wires/leads and paste on connectors for obtaining electrical signals through the skin. Additionally, in this scheme a device such as a cellular telephone/mobile device is enabled for providing an ECG, electro cardiogram of the heart activity.

FIG. 7 shows a system level architecture for wired or wireless networking of an intelligent personal health management appliance for an electrocardiogram evaluation of the heart. The appliance is able to operate in a standalone manner or in conjunction with an RF ID Tag, a local server, a central server and a network server utilizing processing, storage, software and databases contained there in; the system herein using paste on connectors with the ability to transmit the acquired electrical signals remotely via a transmitter attached to each connector. Additionally, in this scheme a device such as a cellular telephone/mobile device is enabled for providing an ECG, electro cardiogram of the heart activity.

FIG. 8 shows a system level architecture for wired or wireless networking of an intelligent personal health management appliance for measuring blood pressure/pulse rate. The appliance is able to operate in a standalone manner or in conjunction with an RF ID Tag, a local server, a central server and a network server utilizing processing, storage, software and databases contained there in; the system herein using a standard cuff and inflation/deflation or a paste on blood pressure/pulse rate sensors with built-in transmitters for transmitting the data remotely of the appliance. Additionally, in this scheme a device such as a cellular telephone/mobile device is enabled for providing real time blood pressure measurement and monitoring.

FIG. 9 shows a system level architecture for wired or wireless networking of an intelligent personal health management appliance for measuring the girth of an individual. The appliance is able to operate in a standalone manner or in conjunction with an RF ID Tag, a local server, a central server and a network server utilizing processing, storage, software and databases contained there in.

FIG. 10 shows a system level architecture for wired or wireless networking of an intelligent personal health management appliance for measuring the height of an individual. The appliance is able to operate in a standalone manner or in conjunction with an RF ID Tag, a local server, a central server and a network server utilizing processing, storage, software and databases contained there in.

DETAILED DESCRIPTION OF THE PREFERRED EMBODIMENTS

Figure 1:
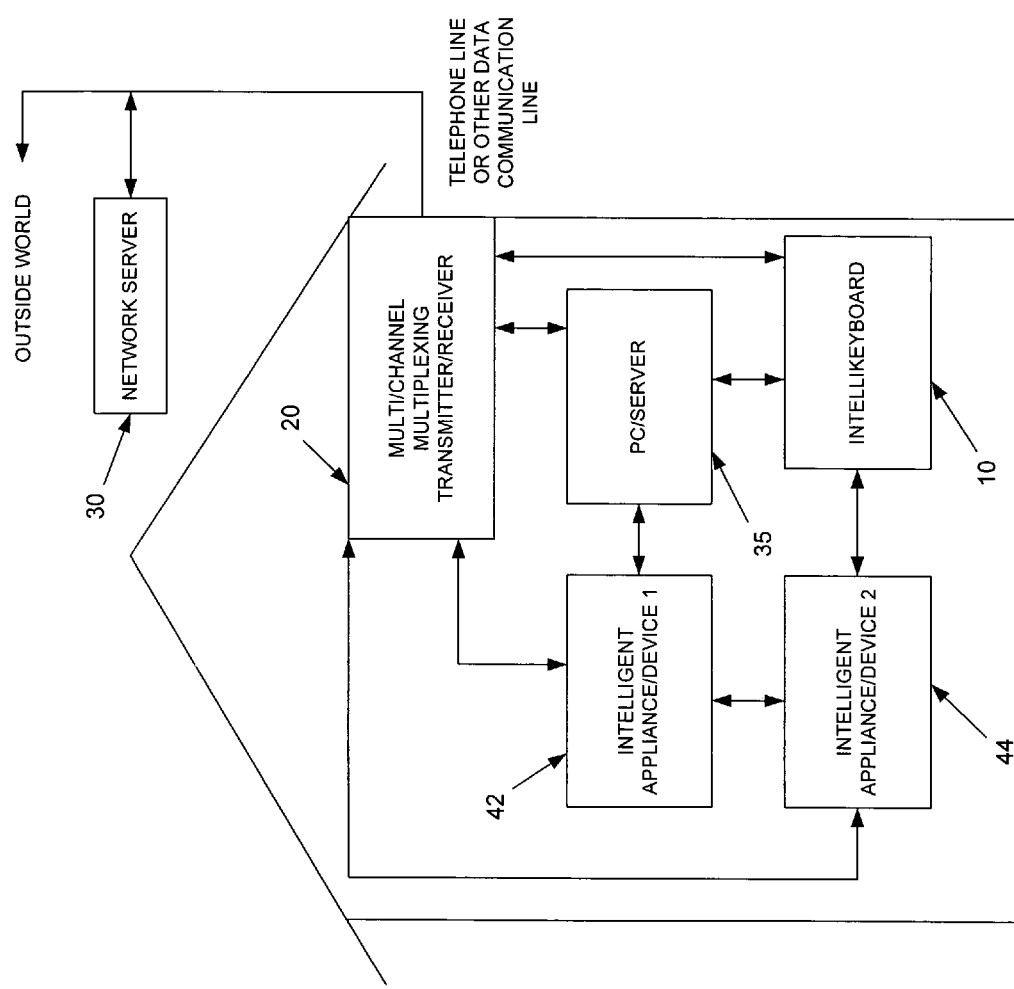

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

For example, the embodiments that follow relate to a networking architecture, a system and apparatus for enabling personal health management in conjunction with different intelligent appliances that are mobile and or wireless, but are intended to include stationary units as well, such as personal computers (PCs) and stationary intelligent and non intelligent appliances; wherein as an illustration a non intelligent appliance is enabled with an external wireless capability and external networking capability by means of attachments and other methods.

Further, the personal health management inquiry or request can be in any form of intelligence, such as key entries from a keyboard, voice in any language, graphics such as a key click on a graphic page, mouse clicks on a view, or even tactile responses or depressions of a foot pedal. Required translations, such as from one language to another or from a tactile entry to a voice command, are made automatically.

As another example, personal health management is enabled in conjunction with one or more types of information including user profiles, appliance profiles, gastronomic information, one or more personal and/or common databases, storage, processors and software resident on one or more devices/servers located within the device itself, a local server, a central server, a network server or located across a network including the Internet. The architecture system and apparatus may have other applications, for example in a hospital/institutional/professional/transportation environment, and the embodiments described herein are for illustrative purposes and are not to be construed as limiting the present invention.

The present invention is a personal health management system comprising of various types of intelligent personal health management appliances that are designed and used for specific personal health management applications. The intelligent personal health management appliances are used in a standalone manner or in conjunction with various gastronomic inquiry and information systems, since the health of an individual generally pivots around the ingestion of food, ingestion of other substances, physical activities and mental activities.

The intelligent personal health management appliance is configured for the real time acquisition of various data related to the individual, storing the acquired data within said appliance and or on a central server, displaying the selected information on said device or another display device, making an information inquiry including health factors and gastronomic factors to an information server having a personal health and gastronomic database. The present invention includes displaying a response to the inquiry related to personal health and gastronomic information from the information server/central server on the selected display device including the intelligent personal health management appliance.

The present invention also includes sending a personal health and or a gastronomic inquiry from the intelligent personal health management appliance/display device to the information server, preparing the selected personal health/gastronomic response to said inquiry on the information server, and receiving the response to the inquiry from the information server with an intelligent personal health management appliance and other devices that include a cellular telephone/a mobile device.

A preferred embodiment includes formatting the personal health/gastronomic response to the selected inquiry on the display device, and displaying the formatted personal health/gastronomic response to the inquiry on the display device and storing/retrieving said information on one or more databases located on the intelligent appliance itself, on a mobile device such as a cellular telephone, personal digital assistant, lap top computer, other mobile devices, stationary devices and one or more servers such a local server, a central server, a network server and a escrow server.

The escrow server securely stores personal health and other information and provides access to the selected information to selected/permitted individuals/entities at the selected times using permission schemes and authentication schemes as defined by the individual. The escrow server further provides that the underlying permission/authentication schemes are not generally made available to authorized individuals/entities and are executed by the escrow server without revealing or compromising sensitive personal information or the specifics thereof.

In the present invention a user selecting an action to be performed by the intelligent personal health management appliance/a mobile device or a stationary device connects to a central server/other intelligent personal health management appliances of the present invention by wired or wireless means. The central server receives the request for the action, and parses the necessary information to service the information/action request. Reference to the central server is intended to include one or more other servers such a local server, a network server and an escrow server. Any information may be parsed, but will normally include identification (ID) of the user, specific identification information related to the intelligent personal health management appliance, the servers and other devices; information about the selected input/output formats selected, communication protocols selected, language, the basis or type of the action, the number of actions desired, and any parameters that may be pertinent.

The parameters involved may include, for example, inputting a limit on the values for a comparison, such as a limit on a selected health parameter by itself or in relation/conjunction with other parameters including gastronomic parameters. As an example of a parameter, an action related to the intended ingestion of a certain type of food may result in a warning upon comparison with a health parameter specific to the individual such as the cholesterol level.

Another preferred embodiment of the present invention includes a mobile device such as a cellular telephone, personal digital assistant, lap top computer and other mobile devices for enabling the control of one or more intelligent personal health management appliances and servers, for initiating a selected query/action using the user preferred input/output methods, displaying a response to the inquiry from the information server/other intelligent appliances on the display device/mobile device/intelligent personal health management appliance.

The preferred embodiment includes sending the inquiry from the display device/mobile device to the information server. The preferred embodiment also includes preparing a response to the inquiry on the information server. The mobile device is used for receiving the response to the personal health management inquiry from the information server with the display device/mobile device. The preferred embodiment includes formatting the response to the personal health management inquiry on the display device/mobile device/personal health management appliance, and displaying the formatted response to the personal health management inquiry on the display device/mobile device/intelligent personal health management appliance.

In another preferred embodiment of the present invention a mobile device such as a cellular telephone, PDA or other mobile communication devices are additionally enabled for performing one or more functions of an intelligent personal health management appliance. As an example a cellular telephone is enabled for performing the functions of a blood pressure measurement/monitoring appliance for providing real time control over the blood pressure level of an individual, especially in conjunction with the real time ingestion of the various foods ingested by the individual and the physical/mental activities related to the individual.

Similarly, in another preferred embodiment of the present invention, for example a cellular telephone with the appropriate wired or wireless skin contacts is enabled for performing the functions of an ECG, electro cardio gram appliance such that the individual is either continually or at selected time intervals/times obtaining his/her ECG profile and tracking the ECG profile in conjunction with the food, exercise and other activities for real time management of personal health by himself/herself or in communication/association with a selected health professional.

The novel embodiments and teachings of the present invention will be made clear in conjunction with the figures and the descriptions:

FIG. 1 shows a system level scheme for networking of one or more intelligent appliances/devices as represented in the prior disclosure by the common inventors, now U.S. Pat. Nos. 6,169,789 and 6,480,587. The system uses an inside wired or wireless communication path, a mobile device such as an intelligent keyboard 10 having central communication, command and control capabilities for voice and data information; a multi-channel multiplexing transmitter/receiver 20 for enabling communication using a plurality of communication protocols between one or more devices internal to the communication environment and one or more devices external to the environment such as a network server 30; wherein the system further comprises of one or more intelligent appliances/devices 42, a PC/central server 35, an outside wired or wireless communication path and a network server for enabling one or more selected communication, command and control tasks using a mobile device such as an intelligent keyboard that has the ability to operate with one or more selected input/output methods including a standard keyboard, touch screen, display, voice, sound, speech, graphics and other methods.

Figure 2:
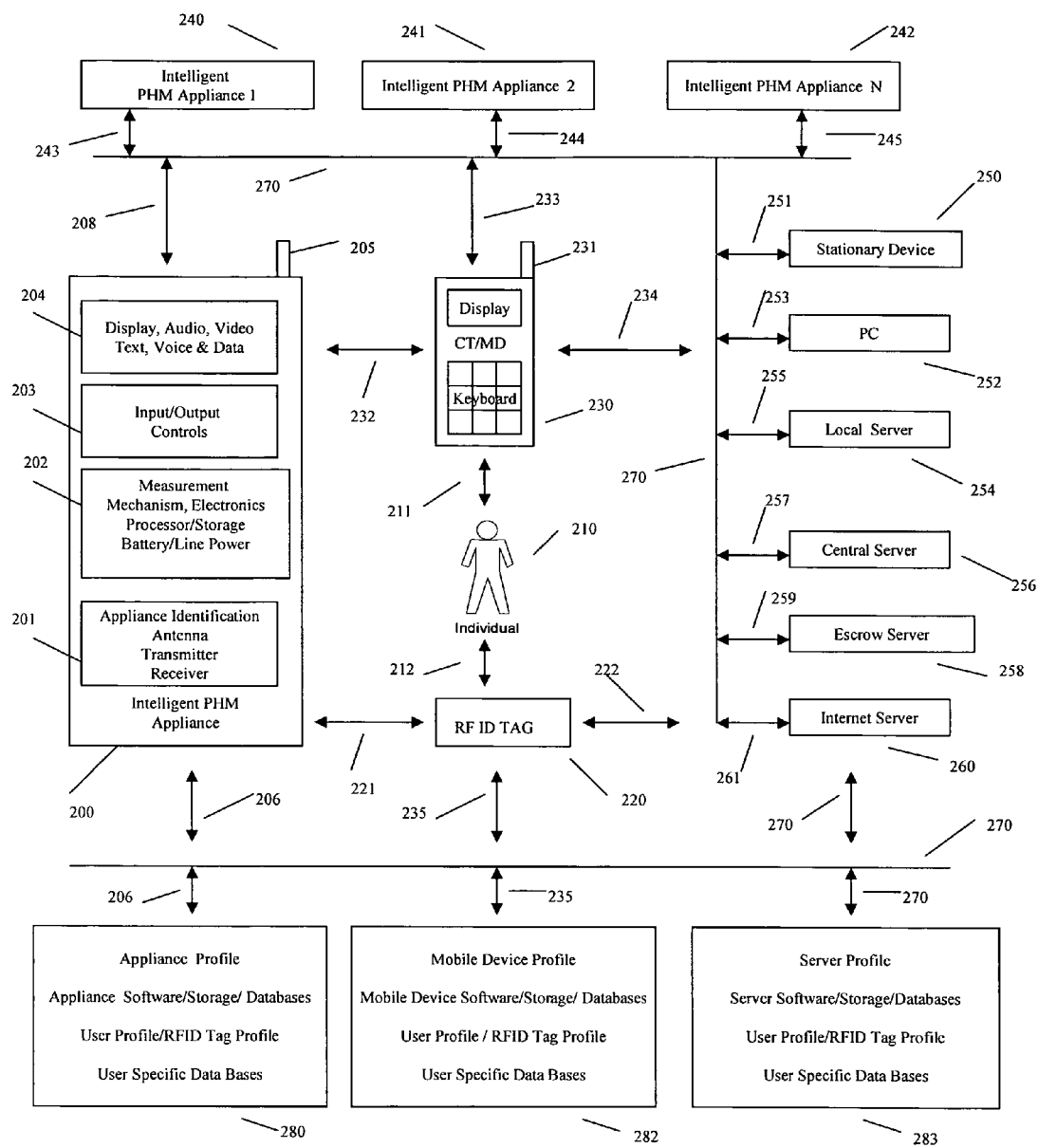

FIG. 2 shows a system level architecture for wired or wireless networking of intelligent personal health management appliances, wherein the intelligent personal health management appliance is able to operate in a standalone manner or in conjunction with an RF ID Tag, a mobile device, a local server, a central server and a network server utilizing the processing, storage, software and databases contained therein. Specifically, the teaching is explained in detail for clear and unambiguous teaching. Additionally, the extensive detailed description is intended for limiting repetition later on with reference to other figures of the present invention as the architecture and system as shown in FIG. 2 is generally applicable to other figures:

The individual 210, is central to the system and represents the person seeking to manage one or more aspects of his/her own personal health including the means for obtaining information, for managing the information and for taking the selected action at the selected time. The individual is enabled for uniquely identifying himself/herself by a plurality of input/output means including voice, speech and text in one or more languages, a unique user ID number, a unique password, biometric methods and other methods.

In a preferred embodiment the individual 210 is uniquely and seamlessly enabled for identification and communication by means of a radio frequency RF ID Tag 220, said RFID Tag containing selected information related to the specific individual 210 including selected medical history and other pertinent information. Further the RF ID Tag 220 is enabled for wearable applications such as on a wrist band, a badge, and other means; and for implanted applications wherein the RF ID Tag 220 is subcutaneously implanted within the selected anatomy of the specific individual 210 for seamless operation in conjunction with the specific individual. The RF ID Tag 220, its relationship to the individual 210, and the ability of the individual to select and set the desired features of the RF ID Tag is represented by the communication and control path 212. The RF ID Tag 220 communicates by wireless means through communication path 221 with the intelligent personal health management appliance/device 200, with other external servers and other personal health management appliances through communication path 222 and with the mobile device through communication path 211. The RF ID Tag 220 comprises of an RF ID Tag profile including information related to the RF ID Tag itself and the individual user, said information being resident within the RF ID Tag itself and/or within a user specific database maintained within a central server, within an intelligent personal health management appliance and within a central server. The communication and retrieval means for accessing the user and RFID specific information is represented by the path 235.

The wired or wireless communication path 270 enables connection 243, 244, 245 between one or more intelligent personal health management appliances 1 through N, such as 240, 241, 242; one or more stationary and server devices such as a stationary device 250, a personal computer PC 252, a local server 254, a central server 256, a escrow server 258 and an Internet server 260. The communication path 251 enables the stationary device 250 to connect with the communication path 270. Similarly, the communication path 253 connects the PC 252, the communication path 255 connects the local server 254, the communication path 257 connects the central server 256, the communication path 259 connects the escrow server 258 and the communication path 261 connects the Internet server 260. The communication methods and protocols may be same or disparate.

Connectivity between intelligent appliances/devices/mobile devices/servers utilizing same and/or disparate communication protocols is enabled by means of one or more enabling devices such as a multi channel multiplexing transmitter/receiver or a similar function device not specifically shown in FIG. 2 and other figures of the present invention but shown in FIG. 1 and incorporated herein by reference to FIG. 1. Additionally, an multi channel multiplexing transmitter/receiver may be included within each intelligent appliance, each intelligent device, a stationary device, a mobile device and servers for enabling communication using one or more channels of communication of said communication device. The multi channel multiplexing transmitter/receiver is incorporated, as applicable, to the architecture of the present invention for a system and apparatus for intelligent personal health management by reference to FIG. 1. Additionally, an intelligent keyboard system may be included in each intelligent personal health management appliance for acquiring biometric inputs and for authentication of said biometric inputs within the appliance itself or in conjunction with a central server and or a mobile device. The intelligent personal health management appliance may also contain a unique RF ID Tag for seamless identification purposes.

The communication path between the intelligent personal health management devices/appliances and the communication path 270 is enabled for same or disparate communication methods and communication protocols. The communication path 243 connects intelligent personal health management appliance 1 to communication path 270. Similarly, the communication path 244 relates to personal health management appliance 2 and the communication path 245 relates to the intelligent personal health management appliance N. The personal health management appliances 240, 241 and 242 may perform similar functions as the personal health management appliance 200, but are preferably intended for performing varied and distinct functions that may be different from the intelligent personal health management appliance 200 for enabling the individual 200 to manage a full spectrum of personal health management activities. As an example the intelligent personal health management appliance 200 may be a blood pressure monitor, the intelligent personal health management appliance 240 may be a ECG monitor, the appliance 241 may be a blood glucose monitor and the appliance 242 may be for measuring weight.

The present architecture/system enables each intelligent personal health management appliance/device to operate with a common communication protocol or a plurality of separate communication protocols that are specific to the selected device, such as Ethernet, Bluetooth, 802.xx and others protocols enabling seamless connectivity and operation. Referring to FIG. 1, one method for enabling contemporaneous communication on one or more channels of an intelligent appliance/device is by incorporating a multi channel multiplexing transmitter/receiver within the appliance/device itself or external to the appliance/device and within the communication environment enabling seamless communication using one or more inside line paths and one or more outside line paths.

The architecture and system of the present invention leverages the communication, computation, command and control capabilities for voice and data information of a mobile device, such as a cellular telephone, a personal digital assistant PDA, a laptop computer and other mobile device, transportable devices and stationary devices for acquiring selected information and for executing selected actions at a selected time in a standalone manner in conjunction with the processing power, storage, software and data bases resident therein; or in conjunction with the processing power, storage, software and data bases resident within a personal computer PC, a stationary device, a local server, a central server, an escrow server and an Internet server or a combination thereof.

Mobile communication devices such as cellular telephones, PDA and laptop computers are increasingly becoming ubiquitous but with limited utility at the present time such as mostly for voice communication and limited data communication. The present invention in novel ways increases the utility of a mobile communication device for a host of applications not conceived in the prior art. The present invention leverages the input/output capabilities of a mobile device for applications in personal health management and for enabling a new class of intelligent personal health management appliances wherein the mobile device itself may be configured as an intelligent personal health management appliance/device, or can be used in conjunction with external attachments, can be used in conjunction with other appliances/devices specifically designed for intelligent personal health management and used in conjunction with a central server. The preferred embodiments of the present invention and the use and utility of the mobile device will become readily apparent with reference to FIG. 2.

Referring now to FIG. 2, the cellular telephone/mobile device abbreviated herein as CT/MD 230, comprises of an antenna 231, a keyboard, a display including a touch screen display, a processor, storage, software and enabling electronics including one or more transmitter/receivers. The CT/MD additionally may include a multi channel multiplexing transmitter/receiver, not shown in the figure, or other implementations for enabling contemporaneous communication of voice and data on one or more input and output channels 232, 233, 234 of the mobile device. The CT/MD 230 communicates with the communication line path 270 and the servers, by means of the wired or wireless communication path 234, wherein the communication protocols on line path 234 may be same or different than the communication protocols of line path 270. Additionally, the CT/MD 230 communicates with one or more intelligent personal health management appliances, 200, 240, 241 and 242 using the wired or wireless communication path 232, 233. The individual/user 210 associated with the CT/MD 230 controls the CT/MD using the path represented by 211. The RF ID Tag communicates with the CT/MD 230 by communication path 212.

Referring now FIG. 2, particularly the functional block represented by 282, the information related to the CT/MD 230, referred in here as the mobile device profile includes the mobile device telephone number, mobile device electronic identification EIN number, mobile IP number, and other information that uniquely identifies the specific unit and its attributes. The mobile device software and software revisions, processing capabilities, storage and data bases resident within the CT/MD 230 are additionally shown in 282 for illustrative purposes as information that additionally describes the CT/MD 230. Further as illustrated in 282, the CT/MD 230 comprises of one or more user profiles related to one or more specific individual users and the associated RF ID Tag profile information related to a specific individual that includes selected identification, medication, medical information and emergency response information. For example the User profile may comprise of user ID, RF ID, user medical history, user dietary and gastronomic preferences, safety and emergency response information. In addition user specific databases are maintained within the CT/MD 230 and or the server.

Similarly referring now FIG. 2, particularly the functional block represented by 283, the information related to the servers is such as the server profile, server ID, server software, server processing capabilities, server storage and data base capabilities are described. The server maintains general databases and user specific databases securely with defined permission levels for accessing this information. Additionally the servers maintain user ID, user profile and RFID Tag profile and RFID Tag related information.

Once again similarly referring now FIG. 2, particularly the functional block represented by 280, the information related to the specific intelligent personal health management appliance/device 200, such as the appliance profile, appliance ID, appliance software, processing capabilities, storage and data base capabilities are described. The appliance 200 maintains general databases and user specific databases securely with defined permission levels for accessing this information. Additionally, the appliance, 200 maintain user ID, user profile and RFID Tag profile and RFID Tag related information. The path for accessing said information is represented by internal/external line path 206.

Once again referring to FIG. 2, a schematic representation of an intelligent personal health management appliance 200 showing various enabling elements contained therein is illustrated. The appliance 200 comprises of a touch screen enabled display and or a standard non touch screen enabled display 204 for the purposes of input/output of data, audio, video, voice including still images and graphics. The input/output/controls 203 enable the appliance 200 to be used in conjunction with one or more selected input and output methods that include as an example voice, speech, text, in one or more languages, key or touch sensitive methods and other methods as preferred by the user. The appliance 200 further comprises one or more measurement and information acquirement mechanisms specific to a selected application such as for measuring weight, measuring blood pressure, measuring electro cardiogram activity of the heart and so on.

The appliance 200 comprises of one or more processors 202 that are application specific or general purpose in nature, appropriate internal storage, user specific data base capabilities, software relevant for a selected application, and specific mechanisms/electronics that enable the selected operation of the appliance. The appliance 200 is uniquely identifiable by one or more methods such as mobile IP, static IP, device ID, RF ID associated with the specific appliance wherein said RF ID is enabled by embedded or attachment means to the appliance 200. The appliance 200 further comprises of one or more antennas 201, 205, one or more transmitters/receivers 201 for enabling single channel or multi channel communication on one or more inputs/outputs 206, 208, 221, 232 of the appliance 200.

The appliance may be enabled with a multi-channel multiplexing transmitter/receiver or other implementations for communicating contemporaneously on one or more input/output channels using one or more selected communication protocols.

The Communication path 208 enables communication between the intelligent appliance 200 and one or more other intelligent appliances such as 240, 241 and 242. The embodiments described for the intelligent appliance 200 are for illustrative purposes and specific intelligent appliances may include all the features illustrated herein or may include additional features or less features and should not be construed as being limited.

Figure 3:
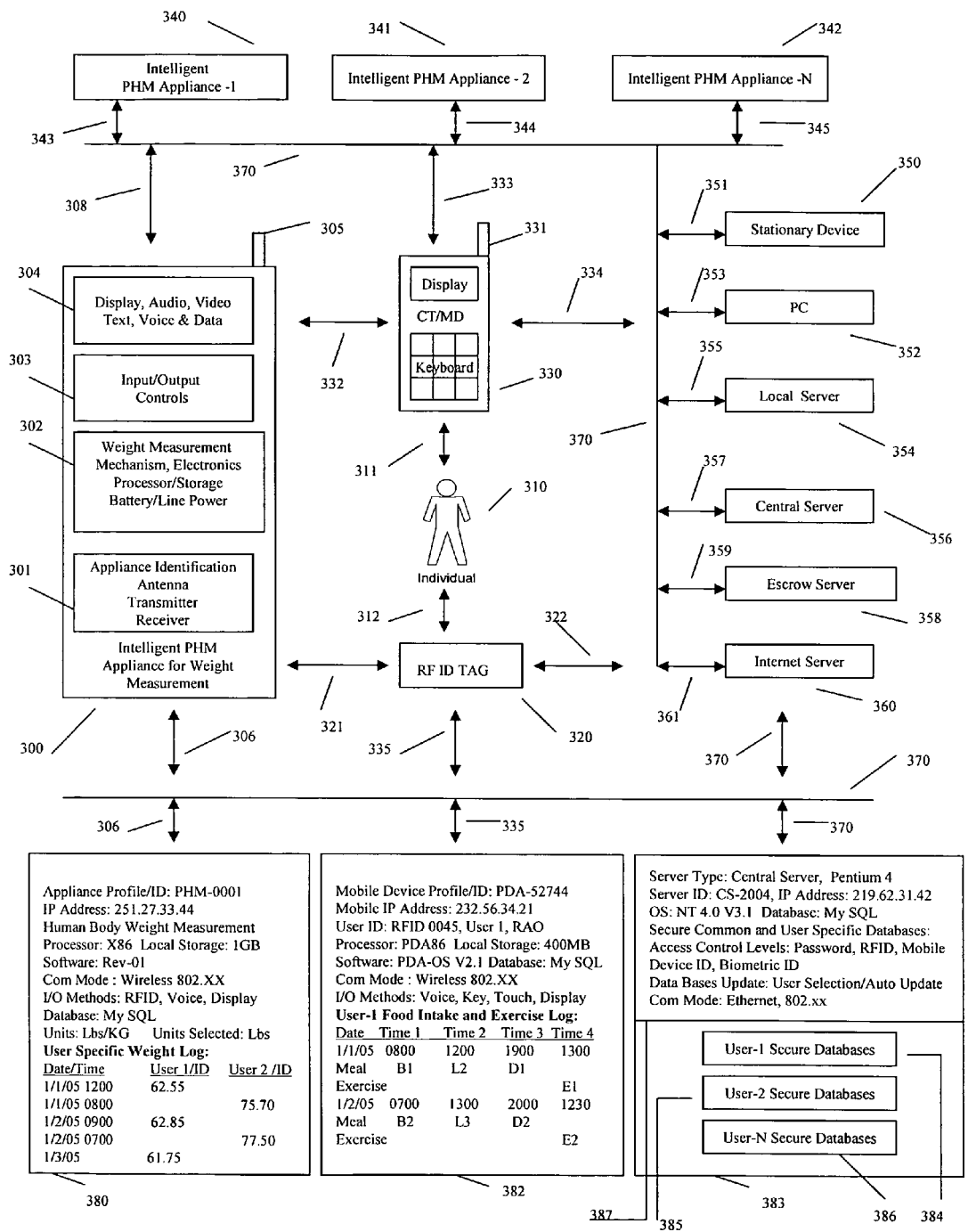

The present invention utilizing the architecture and system as illustrated in FIG. 2 enables a range of varied intelligent appliances for specific and distinct applications relevant to personal health management and other applications. This would be apparent in conjunction with the other figures and the detailed descriptions related to each of said figures:

Referring now to Fig.3 in detail, an intelligent personal health management appliance for the measurement of weight 300, comprises of a functional block 304 enabling display, audio, video, data and voice, a functional block 303 enabling selected input/output and controls, a functional block 302 enabling the measurement of weight in one or more selected units of measurement and a functional block 301 enabling communication by wired or wireless means using one or more antennas 305, one or more transmitters/receivers with confirming/authentication of the appliance identification of both the send and receive appliance/device. A wired or wireless communication path 306 and 308 enabling communication of the appliance 300 with a wired or wireless communication path 370, 343, 344, 345, 351, 353, 355, 357, 359, 361 that includes the capability to communicate with a plurality of other intelligent personal health management appliances 340, 341 and 342; and communication with a stationary device 350, a personal computer 352, a local server 354, a central server 356, an escrow server 358 and an Internet server 360.

In addition the intelligent appliance 300 is enabled for communication with an RF ID Tag 320 associated with the individual user 310 via communication path 321. The RF ID Tag 320 is controlled by the individual 310 by control path 312 and said RF ID Tag is enabled for communication with the communication path 370 via the communication path 335.

A communication device such as a cellular telephone/mobile device CT/MD 330 that communicates with the RF ID Tag 320 via the communication path 331 311 and 312 and 370. The CT/MD 330 enabled for communication with the intelligent personal health management appliance for the measurement of weight 300 via the communication path 331, 332, for communication with one or more servers via communication path 331 334 and 370; and for communication with one or more other intelligent personal health management appliances 340, 341 and 342 via the communication path 331 333 and 370.

The functional blocks 380 relates to the intelligent appliance 300 specific information and secure user specific information including RF ID and CT/MD ID associated with the individual 310 and user specific weight log maintained within the a\intelligent appliance 300. The functional blocks 382 relates to the CT/MD 330 specific information and secure user specific information including RF ID associated with the individual 310, a user profile and user specific weight log, exercise log and other logs maintained within the CT/MD 330. The functional blocks 383, 387 relates to the server specific information and secure user specific information including RF ID associated with the individual 310, mobile device 330 specific information, and user 310 specific weight log, exercise log and other logs maintained within the servers/devices 350, 352, 354, 356, 358, and 360. A plurality of user specific and secure databases, are enabled on one or more servers in addition to user agnostic databases as shown in 384, 385 386.

EXAMPLE 1

Manual Input of User Identification in Conjunction with Weight Measurement

Individual 310 wishing to measure and track his/her body weight uses the intelligent weight measurement appliance 300. Upon activation the individual selects a desired input method such as a user ID number or voice activation method, including speech recognition, for identifying the user as a specifically identifiable person 310 and for selecting a desired action. The appliance 300 recognizes the individual 310 by comparing the input value against the database of identifiable users maintained within the intelligent appliance 300 and/or maintained on one or more servers and a mobile device 330 associated with the individual 310.

The measured value of weight of the individual 310, as expressed in the selected measurement units such as pounds or kilograms is recorded in real time within a user specific weight log/a user specific database maintained within the intelligent appliance 300. Alternately, the information is also recorded in real time or at a selected time in one or more data bases maintained within a mobile device and a selected server. The database maintains other relevant information such as the date, time, user ID and the exact value of the weight. The intelligent appliance 300 is enabled for output such a display on the intelligent appliance 300 or a voice output of the measured value, information about flags such as a weight limit. Alternately, the measured values and analysis thereof such as trends is enabled locally or remotely including on a mobile device CT/MD 330 or on an external display/stationary device 350.

EXAMPLE 2

Using an Implanted or Wearable RF ID Tag as a Primary Identification Means

In this embodiment, upon activation such as standing on the intelligent appliance 300, the intelligent appliance 300 reads and recognizes the specific individual, as individual 310 by communicating wirelessly with the RF ID Tag 320 and determining the user specific information contained within the RF ID Tag 320. The user is enabled for selection of the desired weight measurement and other actions by one or more input methods as illustrated in Example 1. The measured values and other related information is enabled for communication from the intelligent appliance 300 by wired or wireless means to the RF ID Tag 320, the mobile device CT/MD 330, other intelligent appliances 340, 341, and 342; and one or more stationary devices/servers 350, 352, 354, 356, 358 and 360. The weight measurement information and other information is enabled for real time utility or for archival in a database and for utility at a selected time in conjunction with a selected intelligent appliance device/servers.

EXAMPLE 3

Using A CT/MD as a Primary Identification/Control Means and for Transportable Archival of Information A mobile device CT/MD 330 is associated uniquely with a specific individual 310 creating one to one identification scheme between the individual and the mobile device enabling the real time recognition of the individual/the user profile via the mobile device. As in example 2 above, the user is enabled for activation of the intelligent appliance 300 by manual input means, by voice/speech means, by touch screen means, by RF ID Tag means and or by a mobile device means using other methods. A mobile device CT/MD 330 is enabled for communication with the intelligent appliance 300 by wired or wireless communication means. The user using the CT/MD, manually or by automatic means, selects the desired actions of the intelligent appliance 300 and causes the measured value of weight and other information to be communicated back in real time to the mobile device 330, to the RF ID Tag 320, to a stationary device 350, servers 352, 354, 356, 358 and 360; and other intelligent appliances 340, 341 and 342 for real time utility or for archival within one or more databases for contemporaneous use or use at a later time.

EXAMPLE 4

The intelligent weight measurement appliance and other intelligent appliances are additionally configured with an intelligent keyboard system enabling the acquisition of biometric authentication information such as finger print, voice print, retinal scan, hand writing recognition and other information. The acquired biometric information is authenticated within the intelligent appliance itself, authenticated in conjunction with a RF ID Tag, authenticated in conjunction with a mobile device and or a server such as a central server/escrow server.

Obesity is increasingly becoming a silent killer and has become one of the most life threatening conditions. Obesity is closely correlated with the types of foods ingested, the quantities ingested, and the frequency with which the foods are ingested; and obesity is also related with the level of activity such as exercise and stress. The present invention teaches a comprehensive and novel method for measuring and tracking body weight in real time and for correlating the body weight to other parameters.

The ability to measure and archive different types of information relating to one or more parameters such as weight, blood pressure, exercise and the different types of foods ingested and other gastronomic information is invaluable for determining various user specific trends and correlations; for comparing information related to the specific individual with other similar/dissimilar demographic groups, for informed decision making, and for intelligently managing an individual's personal health in real time. The present invention teaches a novel intelligent appliance for measuring body weight and for using said information seamlessly using a communication device such as cellular telephone/mobile device.

Figure 4:
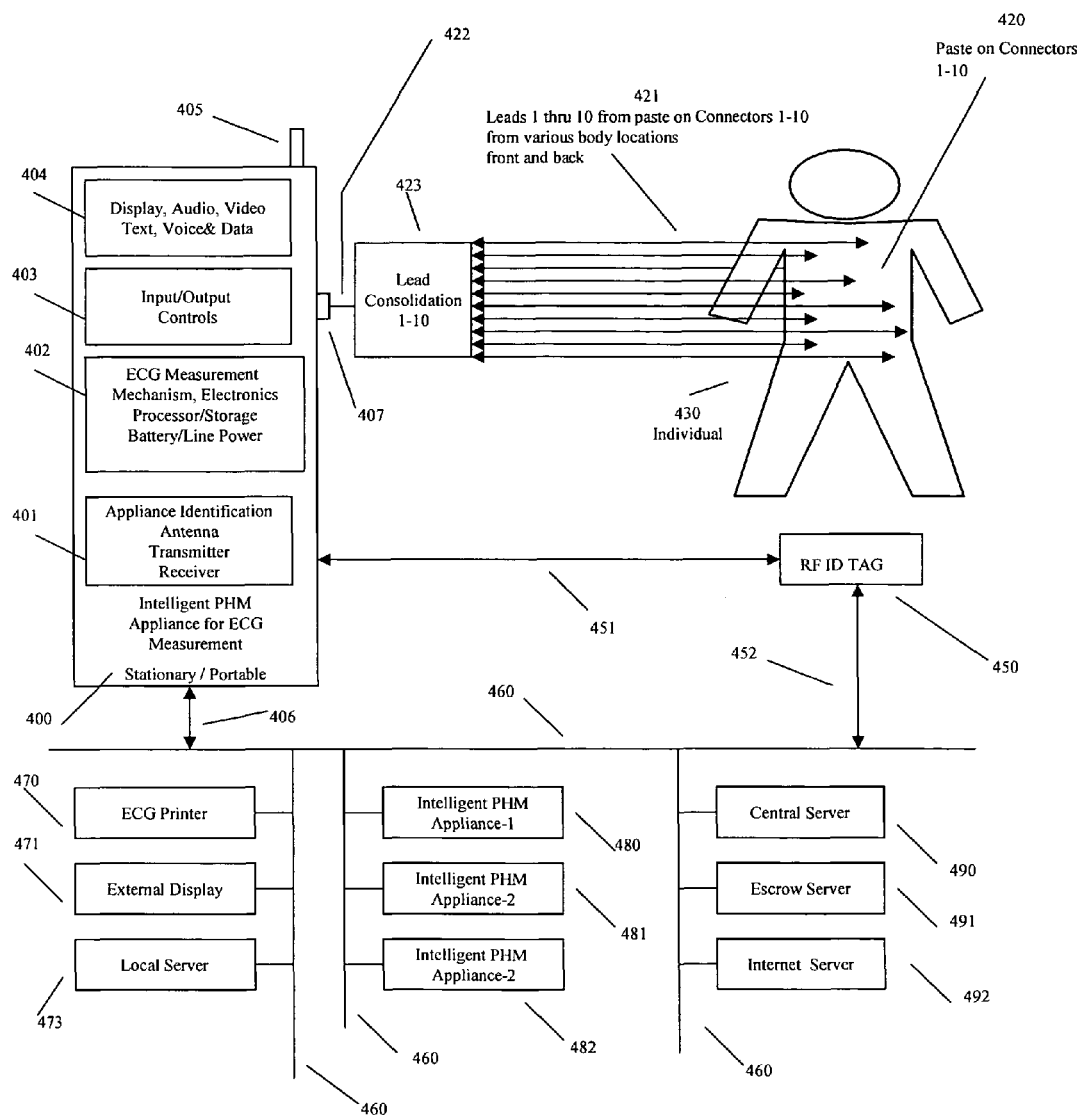

Referring now to FIG. 4, in this particular embodiment an intelligent personal health management appliance for acquiring an electro cardio gram, ECG of the heart is illustrated. This intelligent ECG appliance 400 comprises of one or more antennas 405, a connector slot 407 for plugging an external consolidated cable 422 that provides electrical signals through a lead consolidator 423, wherein the individual leads numbering 1 through 10/N are consolidated into one cable bundle for easy plug in to the intelligent appliance 400. For illustrative purposes ten leads are shown but the number of leads may be more or less depending on the specific application. Typically for a standard ECG ten leads are used and at times 12 leads are used for improved resolution and information. The leads 421 are wired and are attached to equivalent number of paste on connectors 420. The paste on connectors 420 are pasted on the skin at different locations of the torso, on the front and back to acquire electrical signals generated by the heart of the individual 430 through the individual's skin. Additionally, the intelligent ECG appliance 400 comprises of a functional block 404 that enables display of graphics, data and other information, a functional block 403 that enables selected input/output methods and control, a ECG measurement functional block 402 comprising of one or more processors, storage, software and databases.

The measurement system electronics converts the analog electrical signals acquired from each lead to digital data for generating an electro cardio gram of the heart in conjunction with the signal processing capability of one or more processors. The electronics further comprises of a plurality of A/D converters or analog to digital converters and as needed some D/A converters or digital to analog converters, enabling the conversion of the acquired analog electrical signals for further processing by the measurement electronics. The processed information is displayed as an electro cardiogram depicting the electrical and physical activity of the heart from various perspectives for determining the health and condition of the heart. The ECG is enabled for display on the intelligent ECG appliance itself or on an external display 471 or on a stationary device. Further the ECG is enabled for printing on an ECG printer 470 or other remote printers.

The intelligent appliance 400 additionally comprises of one or more transmitters/receivers 401 enabling the unit to communicate using one or more communication protocols with other devices and servers through communication path 406 and 460. A RF ID Tag 450 is used for uniquely identifying the individual. The RF ID Tag 450 contains user specific information including user ID and other medical information. The intelligent ECG appliance communicates with the RF ID Tag 450 via the wireless communication path 451 to acquire the selected information and is also enabled for writing selected information onto the RF ID Tag 450. The RF ID Tag 450 communicates with other devices and servers through communication path 452 and 460.

The intelligent ECG appliance is enabled for communication with other intelligent appliances 480, 481 and 482 and with a local server 473, a central server 490, an escrow server 491 and an Internet server 492, via the communication paths 406 and 460. The intelligent ECG appliance 400 is enabled for acquiring information from one or more databases resident on other devices/servers and for storing information onto said databases. The intelligent ECG appliance 400 is enabled for use in stationary and portable applications.

The ability of the individual to obtain an ECG profile of the heart at a selected time and in a selected location is critical to getting timely attention and for survival. In this embodiment the critical information including the heart medications and emergency instructions are enabled by the RF ID Tag and or the mobile device; the information is readily available remotely and is enabled for use in conjunction with other health factors such as blood pressure, diet and exercise to comprehensively manage the individual's total health over time or instantaneously under emergency conditions.

Figure 5:
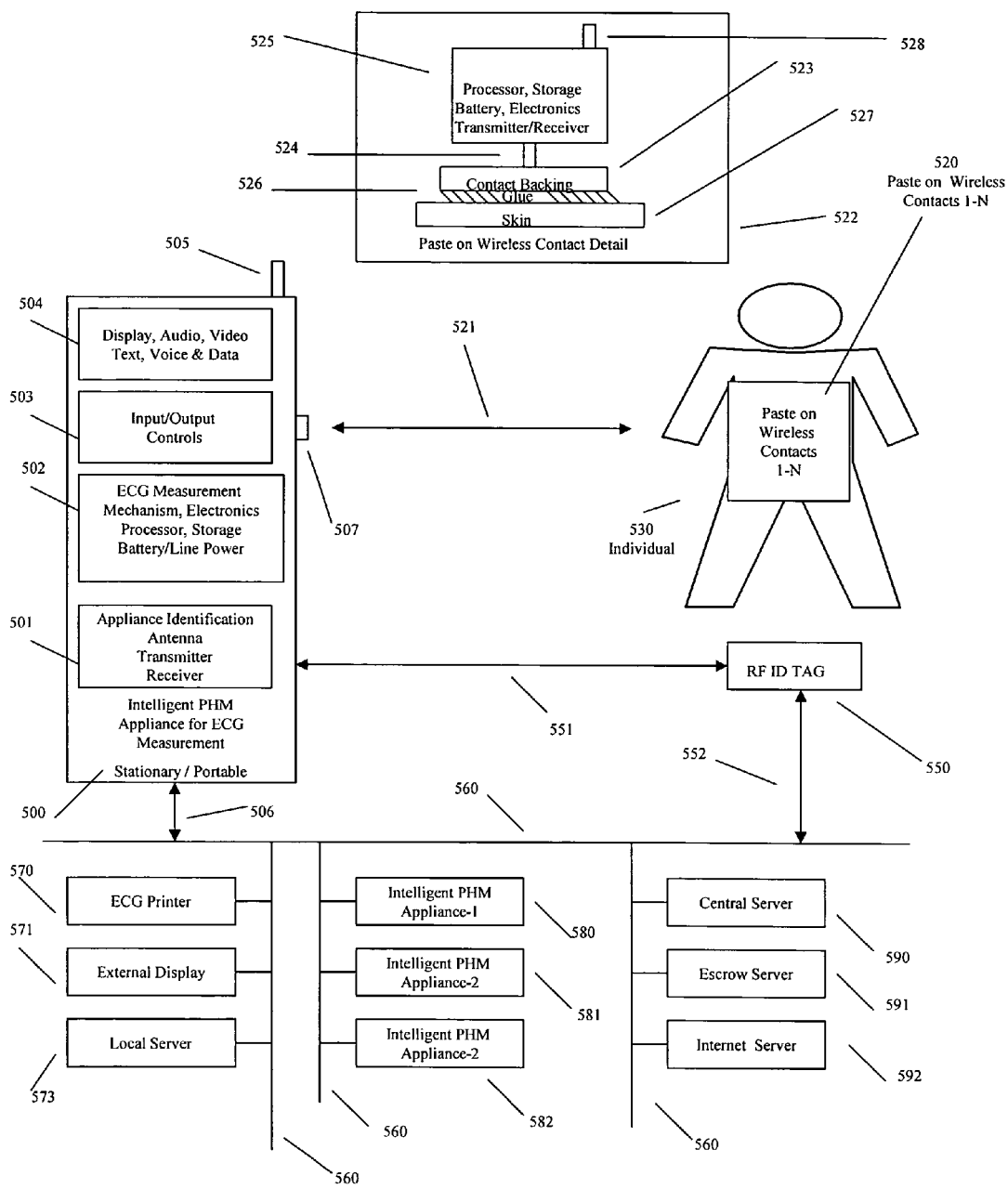

Referring now to FIG. 5, in another embodiment of the present invention relating to the heart, an intelligent personal health management appliance for acquiring an electro cardio gram, ECG of the heart is illustrated utilizing paste on contacts configured with wireless transmitters instead of wired leads. In the prior art, the design and use of wireless skin contacts that acquire electrical signals and transmit said signals wirelessly to a remote device/server is not disclosed.

The intelligent ECG appliance 500 comprises of one or more antennas 505, a connector slot 507 for plugging an external consolidated cable or other external inputs. The paste on wireless contacts 520, numbering 1 through N are pasted on the skin at different locations of the torso, on the front and back to acquire electrical signals generated by the heart of the individual 530 through the individuals skin. Each paste on wireless contact 520 is configured with the electronics needed for acquiring the electrical signal from the skin, for processing said electrical signal internally within the wireless contact system and wireless transmitting the electrical signals from each contact location on the body to the ECG appliance 500 and or other appliances/servers.

Wireless Contacts with Transmitters/Receivers:

The detailed functioning of the wireless contacts 1-N is illustrated by further reference to the functioning of a typical wireless contact system of the present invention as shown in the block diagram 522 of FIG. 5. The wireless contact system 522 comprises of a flexible contact backing 523 that may be made of plastic, rubber or some other material that fits the contour of the specific location of the body at which the contact is pasted on. The contact backing 523 is coated with a conductive adhesive 526 such that the electrical signals picked up from the skin 527 are conducted via the metal nub 524, which is a part of the contact backing 523, and on to the electronic assembly 525. The metal nub 524 attaches to the electronics assembly 525 which includes the electronics for acquiring and processing the electrical signal and the transmitter/receiver including an antenna 528, or alternatively it may include the transmitter only or the receiver only depending on the specific application. The assembly further includes a battery that provides the required power. Whereas the contact backing 523 is easily disposable and used only once per patient the electronic assembly 525 may be repeatedly used with new contact backings 523. Consequently in the present invention a wireless contact system is enabled to alleviate the problems associated with unwieldy multiple leads hanging from several body locations.

The electronics assembly 525 is enabled to acquire and transmit the analog electrical signal acquired from the skin to the remote ECG appliance 500 and or other appliances/servers as analog transmissions. Alternately, the electronics assembly 525 converts the acquired electrical signal to a digital form using one or more analog to digital, A/D converters located within the wireless contact system 525. The various wireless contacts 520, namely contacts 1-N, wirelessly transmit said original electrical analog signal/converted digital signal remotely of the paste on contacts 520; and when in detail viewed for a specific wireless contact 522 via the electronic assembly 525, using communication path 521, to an intelligent ECG appliance 500, other intelligent appliances 580, 581, and 582, a mobile device such as a cellular telephone and or one or more servers 573, 590, 591 and 592. The ECG appliance 500 is enabled to process the signals received using its own on board electronics and software to render an electro cardio gram of the individual's heart in conjunction with the software resident therein. The communication protocols for transmit/receive using wireless contacts 520, 522 and the electronic assembly 525 may be enabled with communication protocols that would not interfere with the functioning of the heart and or other intelligent appliance. The ECG appliance 500 may be configured with a multi channel multiplexing transmitter/receiver or other implementations that enable the appliance 500 to contemporaneously transmit and or receive data using multiple wired or wireless communication protocols on one or more channels of the ECG or other intelligent appliances.

Additionally, the wireless contact system and its associated electronics 525 of the present invention may receive a digital or analog signal from an external source and use said analog signal directly or convert the analog signal to digital, convert the digital signal to analog and combinations thereof The system 522 of the present invention is intended to include a low power battery power source and in selected applications a safe voltage line power, for enabling the wireless contact assembly 525 to function.

Additionally, the system 525 of the present invention may also include a battery power source that may provide a controlled high voltage or high energy pulse of a fixed or variable intensity and time duration for one or more related and or other applications such as in performing the functions of a defibrillator.

The intelligent ECG appliance 500 comprises of a functional block 504 that enables display of graphics, data and other information, a functional block 503 that enables selected input/output methods and control, a ECG measurement functional block 502 comprising of one or more processors, storage, software and databases.

In the case where the analog signal is received, the ECG unit 500 system electronics converts the analog electrical signals acquired from each wireless contact to digital data for generating an electro cardio gram of the heart in conjunction with the signal processing capability of one or more processors resident within the system 500. The electronics further comprises of a plurality of A/D converters or analog to digital converters and as needed some D/A converters or digital to analog converters, enabling the conversion of the acquired analog electrical signals for further processing by the measurement electronics. The processed information is displayed as an electro cardiogram depicting the electrical and physical activity of the heart from various perspectives for determining the health and condition of the heart. The ECG profile as a graph or in other forms is enabled for display on the intelligent ECG appliance itself or on an external display 571 or on a stationary device/mobile device. As an example, with a 12 point wireless contact ECG study, the pertinent information that may be recorded and displayed is aVR, V1, V4 on one graphical line, aVL, V2, V5 on another graphical line, aVF, V3 and V6 on another graphical line, and V5 on another graphical line wherein the symbols and representation relates to the activity of the heart at several regions of the heart and its efficacy. Further the ECG is enabled for printing on an ECG printer 570 or other remote printers.

The intelligent appliance 500 additionally comprises of one or more transmitters/receivers 501 enabling the unit to communicate using one or more communication protocols with other devices and servers through communication path 506 and 560. A RF ID Tag 550 is used for uniquely identifying the individual. The RF ID Tag 550 contains user specific information including user ID and other medical information. The intelligent ECG appliance communicates with the RF ID Tag 550 via the wireless communication path 551 to acquire the selected information and is also enabled for reading only and or writing selected information onto the RF ID Tag 550. The RF ID Tag 550 communicates with other devices and servers through communication path 552 and 560.

The intelligent ECG appliance is enabled for communication with other intelligent appliances 580, 581 and 582 and with a local server 573, a central server 590, an escrow server 591 and an Internet server 592, via the communication paths 506 and 560. The intelligent ECG appliance 500 is enabled for acquiring information from one or more databases resident on other devices/servers and for storing information onto said databases. The intelligent ECG appliance 500 is enabled for use in stationary and portable applications without the individual having to wear leads that limit motion or get tangled. Often there is a need for obtaining an ECG at rest and under exercise stress test. The wired contacts or leads of the prior art are a significant impediment in exercise stress test such as on a tread mill. Similarly the leads present a problem in the event an MRI, magnetic resonance imaging is performed in conjunction with radio isotope injection and imaging such as in a myocardial perfusion heart study.

Additionally a mobile device such as a cellular telephone having significant processing, storage and data base capabilities is enabled for use as a portable ECG machine. The mobile device is configured with the requisite number of A/D converters to convert the electrical signals received from the wireless contact 520. In the case where the mobile device is not configured with on board A/D or analog signal conversion capability such as a standard mobile device, in that case the paste on contacts with a wireless transmitter configured with on board analog to digital conversion capability within said assembly 520 is utilized.

Defibrillator Implementation:

While a specific figure for a defibrillator application is not shown to avoid repetition, it is enabled with specific reference to FIG. 5. The defibrillator function is enabled by providing electrical energy of a selected energy/power level/voltage/current level or intensity delivered for a selected duration upon sensing certain patterns of undesirable heart activity wherein said undesirable heart activity necessitates an external delivery of a controlled electrical energy pulse for stimulating a selected heart activity. The defibrillator function is enabled by an intelligent defibrillator appliance that operates in a manner similar to the functions of an intelligent ECG appliance with the additional capability of providing external electrical stimuli via for example a wireless contact system pasted on various locations of the torso. The electrical stimuli are delivered in conjunction with the intelligent defibrillator device or the mobile device performing the additional functions of an intelligent defibrillator appliance. The control actions for providing real time stimuli to the heart of electrical pulses, is enabled by the intelligent defibrillator appliance by itself or in conjunction with an external server/intelligent appliance where the protocols appropriate for the specific individual are resident. The defibrillation actions are controlled in conjunction with the real time ECG data for providing a comprehensive real time solution to the individual suffering from abnormal or life threatening heart activity/myocardial infraction. Additionally, by continuously wearing the paste on wireless contacts that can provide the electrical impulse needed, the individual is instantaneously able to get real time attention/action using a specifically designed wearable intelligent defibrillator appliance or a combination of an intelligent ECG plus defibrillator appliance. Further the mobile device such as a cellular telephone or other wearable mobile devices can be configured with the appropriate power sources and the software for performing the additional functions of an intelligent defibrillator appliance specifically tailored to the individual.

Figure 6:
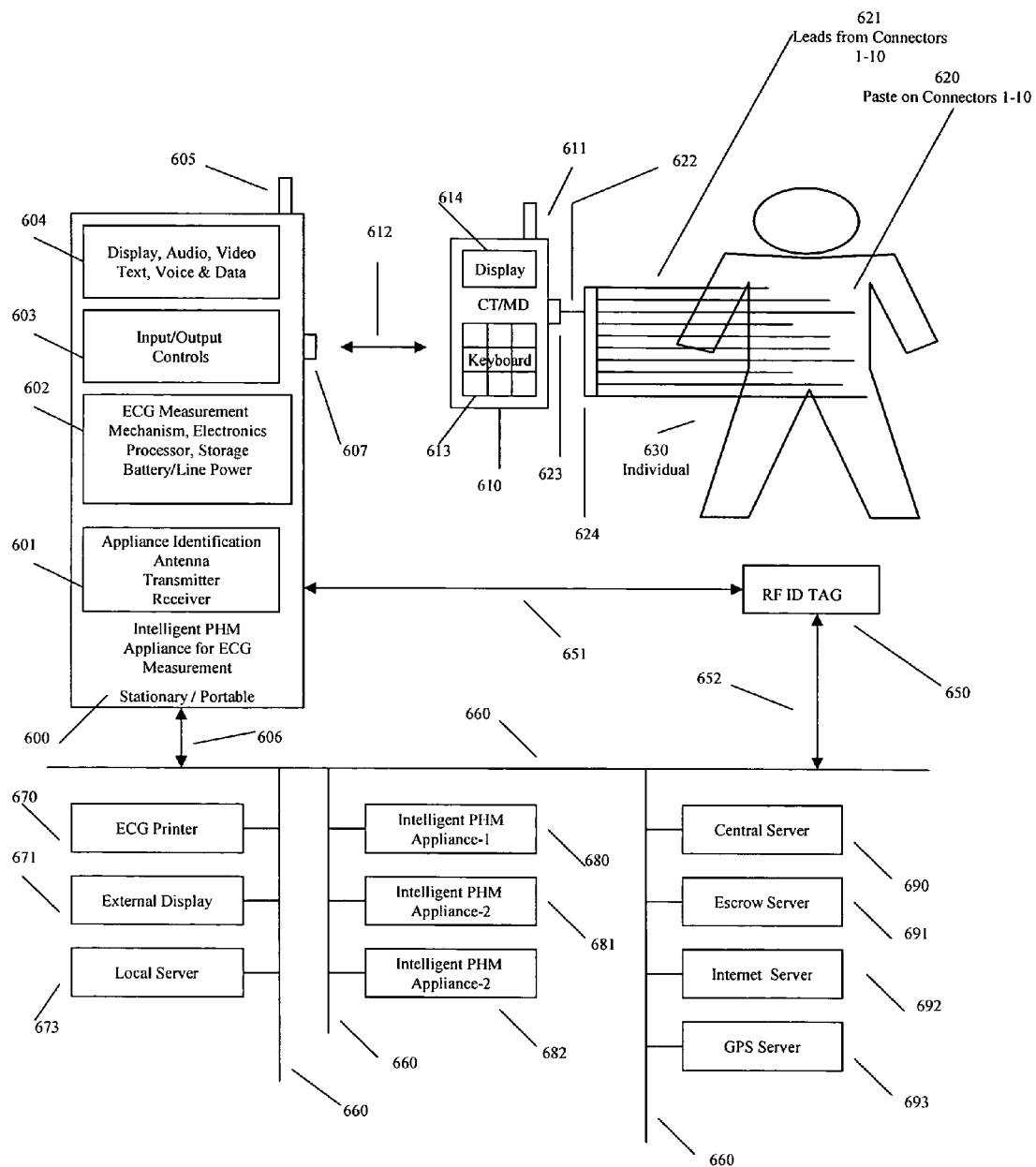

Referring now to FIG. 6 in detail, there is a real need for utilizing a cellular telephone/mobile device as an ECG machine/appliance or as an intermediary device that transmits/receives the ECG data and results from a stationary or portable ECG appliance. The ability of the individual to obtain an ECG profile of the heart at a selected time and in a selected location is critical to getting timely attention and for survival. Getting attention within 10 to 20 minutes of a heart attack is crucial beyond that the chances for survival diminish significantly.

Hence there is a need for the individual to quickly communicate his/her location and or discover the location of the nearest health care facility that has the requisite cardiac care facilities and other facilities. The mobile device that the individual is carrying on the person is enabled to provide the exact location of the individual in conjunction with the global positioning system, GPS server 693 of the present invention. In addition the system is enabled to provide the directions and estimated travel time to/from the health care facility to the specific RF ID Tag/mobile device/individual.

Often individuals can not discern/differentiate heart burn and other conditions related to diets from an adverse heart condition. Consequently, there is a need for enabling a mobile device 610 to perform the functions of a mobile/portable ECG machine or a mobile/portable defibrillator and for also keeping track of the foods ingested in real time.

For the sake of brevity, the essential elements of FIG. 6 are similar to FIG. 4 and are inferred by reference to FIG. 4, except that in this configuration a mobile device 610 is used as a mobile ECG appliance and or as an intermediary appliance/device for transmitting the data to a remote ECG machine 600 and or other intelligent appliances/servers. The mobile device is also used for receiving data from other sources and generally for two way or multi way communications with one or more intelligent appliances/servers using one or more channels of communication available on the mobile device.

In this configuration the wired leads 621 are used with paste on connectors 620. The leads are consolidated by 624 and are plugged into the mobile device 610 via the socket 623. The mobile device 610 communicates by wired or wireless means 606, 607, 612, 660 with the remote ECG appliance 600, 601, 602, other intelligent appliances 680, 681 and 682; servers 673, 690 691, 692 and the global positioning server GPS server 693; the external display 671 and the external printer 670.

Additionally, the individual 630 is enabled to use key inputs including macro key inputs/ voice commands including macro voice commands and the display 614 for viewing the results locally. The ECG results are thus utilized locally or remotely by a health professional via a server. The individual is uniquely identifiable by voice/speech pattern recognition, RF ID 650, 651, 652, finger print, retinal scan and other methods, where in said private biometric authentication information is maintained on the escrow server 691, which securely authenticates the individual without providing the base data to other servers and entities maintaining a very high level of security and privacy. The user/or some other individual in the event of incapacitation such as a heart attack, simply pastes the connectors on the indicated locations on the body of the individual, plugs the leads/lead consolidator into the socket 622 of the mobile device and initiates the ECG by taking detailed actions through key pad, voice or touch screen command means.

Figure 7:
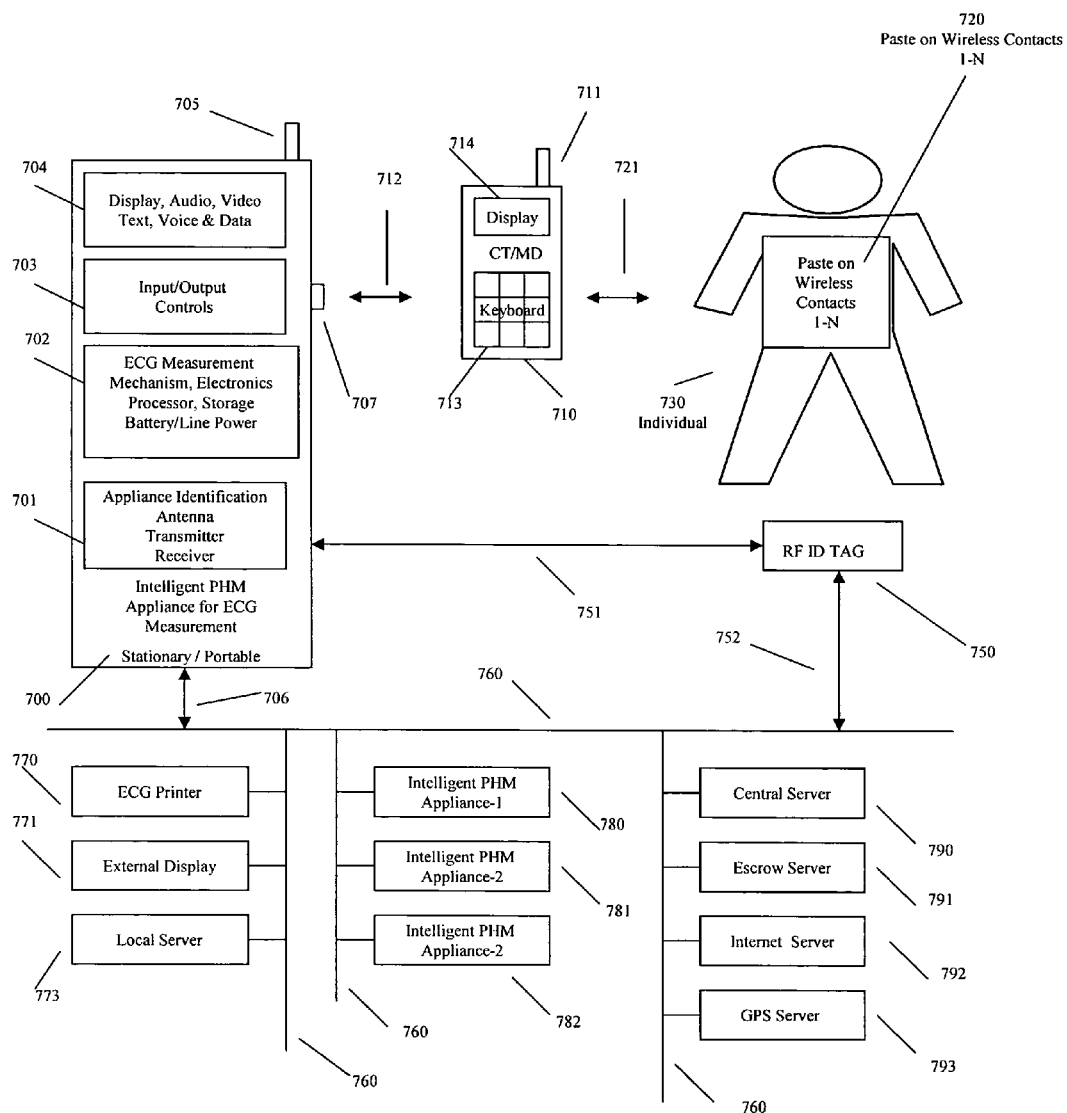

Alternately, a macro command such as by pressing a single key is enabled for obtaining a quick ECG. In the event of sudden disability the finger print of the individual may serve as a macro command for obtaining emergency response specific to the individual in conjunction with the knowledge of the specific location of the individual via an escrow server and a GPS server respectively. The individual may establish on the escrow server a sequence of emergency action protocols/emergency authentication protocols such that the needed actions pre defined by the individual for different events are initiated either voluntarily by him or involuntarily by him/others. Mobile Device operating as an ECG appliance/as an intermediary appliance for communication with a remote ECG appliance in conjunction with paste on Wireless Contacts:

Referring now to FIG. 7, the essential elements of ECG system are similar to that of FIG. 5 and FIG. 6, with the cellular telephone/mobile device 710 being used in this configuration for obtaining the ECG locally of the individual 730 and or the mobile device used as an intermediate communication device for communicating 706, 760 with a remote ECG machine 700 and other intelligent appliances 780, 781 and 782/servers 773, 790, 791, 792 and 793. An RF ID Tag 750 is associated 751, 752 with the individual 730. The mobile device, which includes a keyboard 713 and antenna 711, communicates by wired or wireless means through communication path 712 and the wireless contacts 720 communicate with the mobile device 710 via wireless communication path 721. The ECG machine 700 includes components 701, 702, 703, 704, 705 and has a socket 707 for plugging in leads if needed. Thus the mobile device is enabled for use with leads and without leads. An external printer 770 and an external display 771 are available in addition to the display 714 of the mobile device.

The application is enabled by the innovative means of a wireless contacts 720 having the means for transmitting the acquired analog or converted digital signals to a wearable ubiquitous device such as a cellular telephone, for processing within the mobile device, for transmitting the ECG information in real time to hospitals and health professionals for prompt and timely attention; and more importantly differentiating between a real heart attack and a simple heart burn caused by acidity and the ingestion of foods that cause heart burn.

In this novel scheme of the present invention, the individual is enabled to wear the wireless contacts all the time on and at the indicated body locations as defined by the health professional for continuous monitoring of the ECG, continuous transmission of the ECG data to a remote health professional, or wear the wireless contacts on an as needed basis. This scheme of the present invention enables the individuals who are prone to myocardial infractions to have full range of motion without the restriction of the leads of the prior art and provides the freedom to travel with the secure knowledge that the individual is continuously or at periodic intervals is being monitored.

According to present estimates nearly 50% of the emergency visits to emergency rooms are for gastric distress and not for real heart attacks or other myocardial infractions. Thus being able to track in real time the foods ingested, the activities indulged in and continuously/periodically monitoring the heart activity by means of an ECG using a cellular telephone/mobile device either configured for the additional functions of an ECG appliance, specifically designed and designated for the purpose of serving as a mobile ECG appliance in conjunction with wireless contacts of the present invention provides the user full range of mobility and freedom to travel. The range of travel can also be monitored continuously by the central server, a GPS server or other intelligent appliances to ensure that the individual is within the range of a selected/prescribed distance/travel time from a health care facility.

Figure 8:
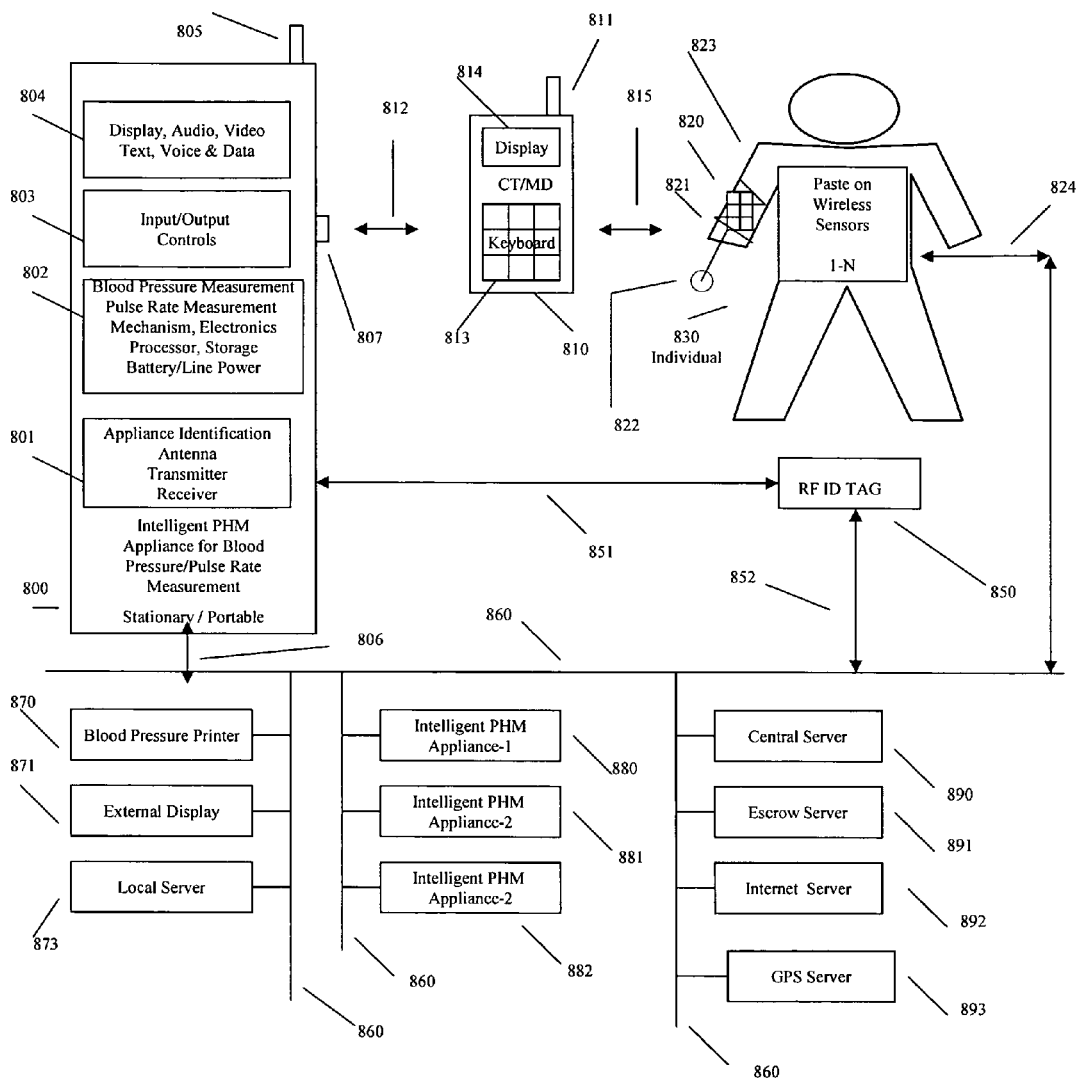

Intelligent Appliances for Measurement of Blood Pressure:

Referring now to FIG. 8 in detail, an intelligent personal health management appliance 800 for the measurement of blood pressure of the present invention comprises of a the functional block 804 enabling display, audio, video, text and data; a functional block 803 enabling one or more inputs/outputs and control functions; a functional block 802 comprising of the mechanical systems, electrical/electronic systems, processors and storage for enabling the measurement of blood pressure, processing of the data and for the storage of the data in a selected media contained within the intelligent appliance itself; a functional block 801 comprising of the means for identification and authentication of the intelligent appliance itself and other intelligent appliances, and an antenna, transmitter/receiver and the extended antenna shown externally as 805. The intelligent blood pressure measurement and monitoring appliance 800 communicates by wired or wireless means using one or more channels of inputs/outputs via communication path 806 and 860 with one or more peripheral devices such as the blood pressure printer 870, the external display 871, the local server 873, other intelligent personal health management appliances 880, 881, 882, the central server 890, the escrow server 891, the internet server 892 and the global positioning server 893. The intelligent appliance 800 further comprises of a port 807 for directly plugging in a blood pressure acquisition system 820 which comprises of a dial/display for indicating the measured value of the pressure in an analog or digital format locally within the system 820 and or on the intelligent appliance 800; cuff 821 wherein said cuff is enabled for wrapping around the arm 823 or some other appendage of the human body of the individual 830 for exerting selected and controlled amount of pressure on the blood vessels and reading the blood pressure upon steady state exertion of pressure and the release of said pressure in a selected manner by manual means by squeezing/releasing the bulb 822. Alternatively and optionally the system 820 comprises of an automatic means for exerting and releasing the pressure in a controlled manner in accordance with the directions and under the control of the intelligent appliance 800. In another feature of the alternate and optional configuration of the system 820, the system 820 comprises of the mechanical, electronics, power supply, transmitters and receivers for receiving control instructions from the intelligent appliance 800, for applying the selected pressure on the arm for a selected time, for reliving the pressure in a selected manner and for measuring a systolic/diastolic blood pressure value and transmitting said data to the intelligent appliance 800 by wireless means from the system 820 so that the system 820 does not have to be plugged directly into the intelligent appliance 800 thus providing the individual with increases degrees of motion. The intelligent blood pressure measurement and monitoring appliance 800 is optionally enabled for receiving 824 collateral inputs related to other human body data from one or more paste on wired/wireless sensors 1-N, pasted on the individual 830.

The individual may choose to wear an implantable or external RF ID Tag 850 that uniquely identifies the individual 830 and the data related to that specific individual. The RF ID Tag 850 communicates by wired or wireless means via communication path 851 with the intelligent blood pressure measurement appliance 800 and by communication path 852 with other servers, stationary/mobile devices 810 and other appliances. The measured values of the blood pressure related to the individual 830 and the times/locations at which said blood pressure values were measured is additionally/optionally enabled for being written onto the RF ID Tag thus providing a real time history that is very valuable for personal health management. The above detailed intelligent blood pressure measurement appliance has great utility in stationary and portable applications such as in a home, hospital or for wearable applications for continuous monitoring and control.

In another novel embodiment of the present invention, the mobile device 810 such as a cellular telephone, PDA or other devices are enabled to perform the functions enumerated for the intelligent blood pressure measurement appliance 800 obviating the need for carrying a separate equipment. In this embodiment of the present invention, the mobile device is configured with a plug in port similar to the port 807 on the intelligent appliance 800. Alternately the mobile device 810 communicates by wired/wireless means 815 with the transmitter/receiver and electrical/mechanical systems of the unit 820 to control the system 820 and acquire the blood pressure measurement values. The mobile device comprises of an antenna 811, a keyboard 813 and a display 814. The mobile device is enabled for communication by wired or wireless means with another intelligent blood pressure appliance such as appliance 800 and other servers via communication path 812. The measured blood pressured values are enabled for processing/storage within the mobile device itself or on one or more servers.

The above detailed descriptions of the present invention with specific reference to FIG. 8 enable the individual to utilize a specifically designed intelligent blood pressure/pulse rate measurement appliance 800 or a ubiquitous communication device such as a mobile device for performing the additional functions of blood pressure measurement. The measured blood pressure values are stored in one or more locations such as on the mobile device itself, on a central server or other databases enabling comprehensive health management of the individual by the individual or by the individual in conjunction with a health professional. Blood pressure is related to the ingestion of different types of foods and therefore the measured vales of blood pressure are now capable of being related to other data contained in one or more databases resident within the mobile device and the servers enabling real time personal health management. In addition, blood pressure varies with anxiety and other activities and mental conditions. The system and apparatus of the present invention enables different types of data to be correlated. In a similar manner, system is also capable of measuring and monitoring the heart pulse rate of the individual. While detailed description has been provided for the measurement of blood pressure, it should be readily apparent that the heart pulse rate is a collateral measurement and is included by reference.

The embodiments of the present invention enable the acquisition of the blood pressure and pulse rate of the individual continuously or at selected times and selected time intervals since the intelligent blood pressure/pulse rate measurement monitoring equipment is wearable or is a mobile device such as PDA, cellular telephone. Additionally, the global positioning features enable the measured values to be related to altitude, altitude changes and other geographical variables providing either data or alerts that are tailored to the specific individual, his/her food habits, medications, physical and mental conditions and prior history.

Figure 9:
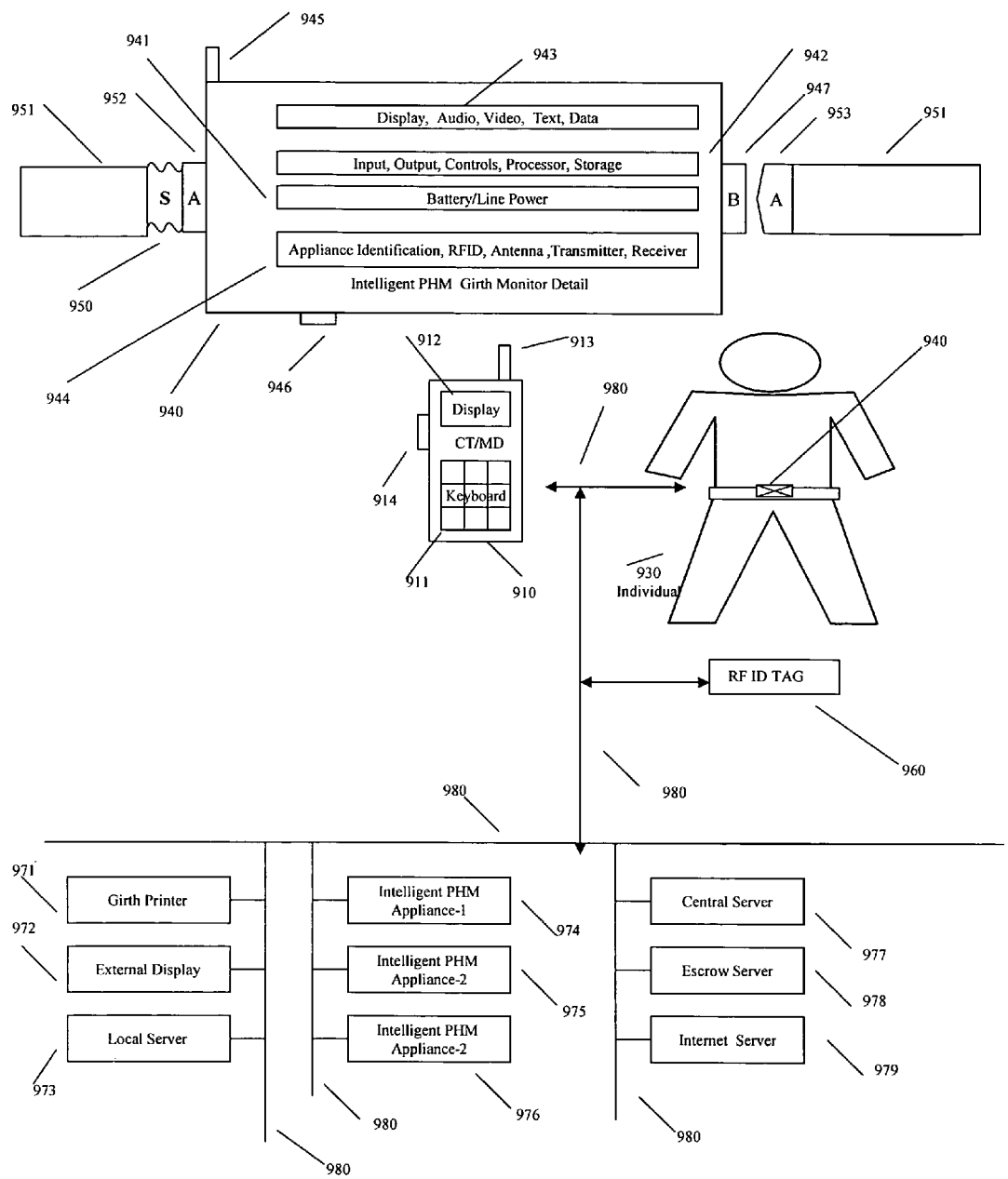

Intelligent Appliance for Measurement of Girth:

Referring now to FIG. 9 in detail, an intelligent personal health management appliance 940, for the real time measurement of the girth of the human body such as around the abdomen/waist is described. The appliance 940 is illustrated for applications around the waist, but is generally applicable for the measurement of the girth of different parts of the body such as the arms, legs and other parts. The Intelligent PHM girth monitor detail is further illustrated in the standalone block diagram labeled 940 which is also intended to show a belt buckle in which the mechanism and electronics is contained, the buckle unit comprises of a functional sub block labeled 944 performing the functions of appliance identification, antenna and transmitter/receiver including an RFID; a functional sub block 941 for battery/line power; a functional sub block 942 for input/output and controls, processor and storage; and a functional sub block 943 for display/audio, video and text. The appliance 940 further comprises of a spring mechanism, S, labeled as 950 providing a calibrated tension level that correlates to the length to which the belt 951 is extended, thus providing a calibrated minimum pressure on the waist to accurately measure the girth without excessive pressure or too little of pressure. One side of the belt 951, labeled as A1 is attached to the measurement mechanism unit 940 enabling communication with the mechanism and electronics contained within unit 940. The other end of the belt 951 comprises of a metallic contact A2, labeled 953. The insertion of the A2 end of the belt into the contact B labeled as 947, of the unit 940 completes the circuit and enables the measurement of the girth with a calibrated pressure being put on the waist for enabling accurate measurement in conjunction with the spring S, 950. The unit 940 further comprises of an antenna 945 and RFID Tag function within functional sub block 944, such that the intelligent girth measurement appliance is enabled for association with a specific individual or is identifiable distinctly if used by more than one individual. The unit 940 further has the capability for external input/output through the port 946. The intelligent girth measurement appliance 940 is enabled for communication by wired or wireless means 980, with other external intelligent appliances 974, 975 and 976; with a central server 977, a escrow server 978 and a network server 979; and with a girth measurement printer 971, an external display 972 and a local server 973 using the wired or wireless communication path 980. The girth measurement appliance 940 additionally is enabled for communication with an RF Tag 960 that is worn by the individual 930 to uniquely identify the individual by means of the RF Tag 960 or by means of the mobile device 910. The RF Tag 960 may be enabled for read only or for read and write functions.

The individual 930 is enabled to wear the intelligent girth measurement appliance 940 for periodic measurements of the individual's girth or alternately is enabled to wear the appliance 940 as a belt such that the girth is monitored and measured continuously or at selected intervals. The expansion and contraction of the waist is measured and is also enabled for correlation with the level of physical activity and the ingestion of different types of food in a short period or over defined longer periods of time. Individual's weight gain is not considered necessarily detrimental to personal health, but when the weight gain results in extended abdomen or paunch then the weight gain coupled with the distribution of the weight over the body is a risk factor. Consequently the girth of an individual is a critical factor in managing personal health risk factors.

The intelligent appliance 940 is enabled for wearing by the individual 930 and further transmits the girth data using wired or wireless communication path 980 to the cellular telephone/mobile device, CT/MD 910, wherein the mobile device comprises of a display 912, a keyboard 911, an external input/output port 914 and an antenna 913. The mobile device is enabled for command and control of the intelligent girth measurement appliance 940 by keyboard, audible, voice and other means and or is enabled for command and control independent of the mobile device 910. The girth measurement data generated by the appliance 940 is enabled for processing and storage internal to the appliance 940, and or for processing and storage internal to the mobile device and or for processing and storage on one or more selected servers and or for use in conjunction with one or more other intelligent personal health management appliances. Consequently, the extended information resident within one or more devices/appliances and servers is co-related in a selected manner. For example the girth measurement is related to weight, to height, to exercise, to the body mass index, to heart activity, to blood pressure, to medications and to the ingestion of different types and the amounts of food. Additionally, the spurious factors such as the variations in girth measurements due to the ingestion of foods that produce gas, bloating and flatulence are enabled for measurement and co-relation for managing a number of other discomfort causing and real risk factors. As an example, individuals with Crohn's disease and with intestinal bowel disorders often suffer from bloating and distended abdomens. Certain medications in addition to foods cause bloating and distended abdomens. The appliance 940 further enables such subtle variations to be measured, monitored and related to foods, medications and other health factors.

Figure 10:
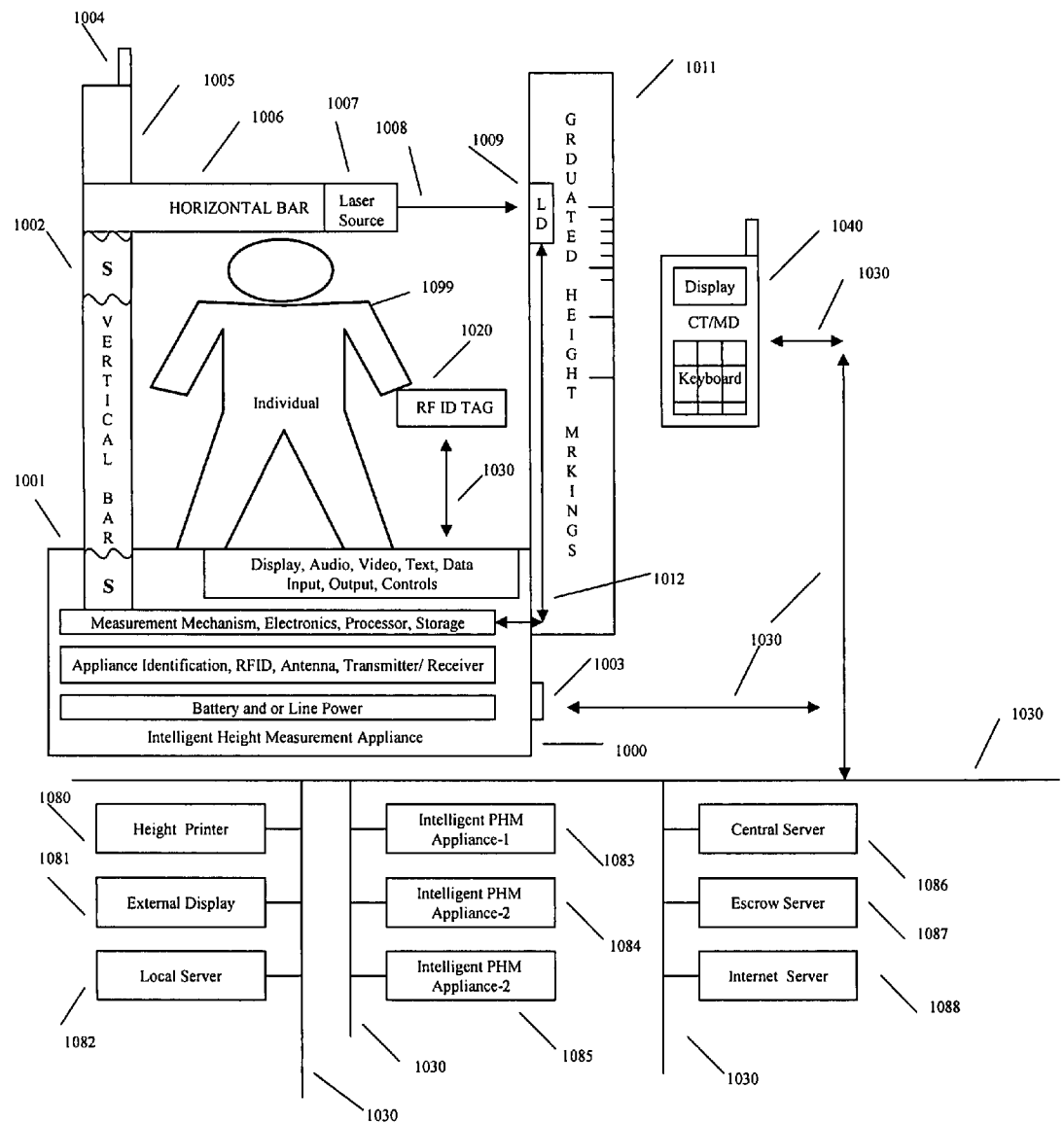

Intelligent Height Measurement Appliance:

Referring now to FIG. 10 in detail, the intelligent height measurement appliance 1000 in one preferred embodiment that measures the height by mechanical means, comprises of a planar base 1001 on which an individual stands for the accurate and precise measurement of height. The appliance 1000 further comprises of internal functional blocks for performing one or more functions such as display, audio, video, text; input, output and controls; a measurement mechanism, electronics, processor and storage; appliance identification including RF ID identification, antenna, transmitter/receiver, with the antenna specifically shown as 1004; a battery and or line power capability; a port 1003 for external inputs/outputs; and a vertical rigid bar 1005 with spring S, 1002 capability at one or both ends of the vertical bar. A horizontal bar 1006 that is parallel to the base 1001 is enabled for movement up or down on a track located on the vertical bar 1005 and is held in position at one or more locations along the vertical bar 1005 by spring loaded means or mechanical means, counter balancing or other means. The horizontal bar 1006 is positioned by manual or automatic means over the top of the head of the individual 1099 and is designed to stop upon encountering a calibrated amount of resistance to motion to enable accurate measurement and to ensure personal safety. Upon sensing a calibrated resistance to the movement of the horizontal bar or upon sensing no motion of the horizontal bar the measurement mechanism determines the height with reference to the planar base 1001. The measured value is processed, stored and or communicated to one or more external intelligent appliances 1083, 1084 and 1085; to the central server 1086, escrow server 1087 and the network server 1088; to the height printer 1080, external display 1081 and the local server 1082. The appliance is enabled for wired or wireless communication by the communication path 1030 such that information is communicated to and from a desired appliance, device and servers including the mobile device 1040 and the RF ID Tag 1020 which contains individual specific information and or on which results of the height measurements can be written into.

The mobile device 1040 is enabled for command and control by keyboard and other means and for processing and storage of the height data in conjunction with other information such as weight, foods ingested, exercise and other information contained in one or more databases within the mobile device, within one or more intelligent appliances, within one or more servers and within the intelligent height measurement appliance 1000 itself The height measurement results may be viewed on the display of the appliance 1000 itself or on the vertical bar 1005 which has graduated height marking in one or more units, or on the mobile device display or on an external display or may be printed. The height of individuals is determined by genetics and to some controllable extent by proper diet as evidenced by the steady increase in height of different populations as a result of improved diets.

In another alternate embodiment of the present invention, referring once again to FIG. 10 in detail, the horizontal bar 1006 is configured with a light source or a laser light source 1007, such that upon steady state gentle resting of the horizontal bar on the head of the individual a beam of light or laser light 1008, is beamed to another vertical bar 1011 on which graduated height markings are provided in one or more units of measurement. The measured values may be visually observed and input by voice or other means into the appliance 1000, the RFID 1020, the mobile device 1040 and other appliances and servers. Alternately in another variation of this particular embodiment, the vertical bar 1011 is enabled with a light detector, LD, 1009 such that the laser/light beam 1008 is detected and consequently the height 1012 is measured. As an example, the light detector 1009 is coupled with the horizontal bar 1006 such that the up and down motion of the horizontal bar 1006 causes a corresponding up and down motion of the light detector 1009 enabling the use of only one light detector and extremely precise height measurements.

Accurate and frequent measurement of height is necessary for pediatric applications. The incidence of obesity in children is significant and the management of the weight in relation to the height of a child is of great importance, especially during the growth stage of children. Proper nutrition ensures that children achieve their full height potential without at the same time suffering from obesity. The ability for children and young adults to use a mobile device such as a cellular telephone, PDA and other mobile devices to proactively track height, weight, nutrition and other factors and maintain detailed data bases for personal health management by his/her self or in conjunction with a health professional is enabled by the present invention. In addition, adults who have achieved full adult height can use the intelligent height and weight measurement appliances to accurately calculate the body mass index, BMI, which is an indicator of proper health and other risk factors that lead to heart infractions and stroke. The monitoring of the height and also the posture of adults is also relevant since the gait, posture and height are functions of factors such as osteoporosis that result in loss of height due to number of factors including bad posture.

The foregoing descriptions of specific embodiments of the present invention have been presented for purposes of illustration and description. They are not intended to be exhaustive or to limit the invention to the precise forms disclosed, and it should be understood that many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A system having a sensor device, comprising:
   a substrate with conductive adhesive material for communicating electrical signals and attaching to a body of a user;
   circuitry coupled to the substrate and acquiring electrical signals representing one or more biological parameters of the body;
   a processor coupled to the circuitry and the substrate, wherein the processor is programmed to generate processed information by processing the electrical signals representing the biological parameters including electrical signals received from a heart of the user;
   an identification device coupled to the processor, the identification device providing device identification data for uniquely identifying the sensor device and user identification data for uniquely identifying the user;
   a database coupled to the processor and configured for carriage on the body, the database storing one or more of the electrical signals, the processed information and health information of the user, the health information selected from the group consisting of gastronomic information, dietary information, physical activity information, exercise information, allergy information, information of ingested food, information of ingested medication, user profile, and emergency response information;
   a transmitter coupled to the processor and transmitting the electrical signals and the processed information representing the biological parameters;
   a power source coupled to the substrate and controlled by the processor to deliver calibrated energy to the body in response to the processed information representing one or more biological parameters such that the energy has a level and intensity sufficient for application through a surface of the body and which is selected by the processor in response to the information sufficient to stimulate a selected heart activity; and,
   a cellular telephone in wireless communication with the transmitter, the cellular telephone having a local processor programmed to initiate a selected query or action with the processor coupled to the circuitry such that the cellular telephone enables control of the circuitry and further having a display programmed to display a response to the query or action from the processor coupled to the circuitry,
   wherein the processor is further programmed to correlate the biological parameters including the electrical signals from the heart and the health information and, in response, render an electrocardiogram representative of the electrical signals and further generate and output a warning when the processed information includes data of an emergency health condition in the user.

2. The sensor device of claim 1, comprising a receiver coupled to the processor, the receiver configured to receive the health information and control and command signals, the receiver configured for wired and/or wireless communication.

3. The sensor device of claim 2, comprising a power source comprising one or more of battery and line power coupled to one or more of the processor, the circuitry, the transmitter, the receiver, and the substrate.

4. The sensor device of claim 1, wherein the biological parameters include information of one or more of cardiac activity, cardiac function, heart muscle function, heart valve function, heart efficiency, vascular function, artery function, an electrocardiogram (ECG), an echo cardiogram, blood pressure, pulse rate, heart rhythm, brain activity and electro-encephalogram (EEG).

5. The sensor device of claim 1, wherein the information of the biological parameters is used for one or more of observation, research study, real time monitoring, periodic monitoring, correlation, diagnosis, treatment, database archival, communication, command and control.

6. The sensor device of claim 1, comprising a memory device coupled to the processor, wherein the memory device is configured to store the information of the biological parameters for one or more of real time utility, utility at a selected time, and utility for a selected purpose.

7. The sensor device of claim 1, wherein the information of the biological parameters is further transmitted to a remote medical device carried by the user, wherein the remote device includes a memory that stores the electrical signals, the processed information representing the biological parameters, and the health information, wherein the remote device includes a processor configured to correlate the information of the biological parameters and the health information.

8. The sensor device or claim 1, wherein the transmitter is configured to transmit using one or more communication protocols.

9. The sensor device of claim 1, wherein the transmitter is configured to transfer the information of the biological parameters to a remote device that includes one or more of a cellular telephone, mobile device, another medical device, a local server, a network server and a RFID tag, wherein the remote device includes a memory that stores the electrical signals, the processed information representing the biological parameters, and the health information, wherein the remote device includes a processor configured to manipulate the information of the biological parameters and the health information, the manipulation including one or more of processing, analysis, correlation, tracking, storing, monitoring, command, control and communicating.

10. The sensor device of claim 1, wherein the electrical signals includes one or more of analog and digital electrical signal information 20 from one or more of the heart, heart muscles, pectoral muscles, arteries, blood vessels, and one or more of different chambers or the heart, different regions of the heart muscle, human tissue surrounding the heart and different regions of the human anatomy.

11. The sensor device of claim 1, wherein the database is in an RFID tag.

12. The sensor device of claim 1, wherein the substrate is configured to provide one or more of flexibility, rigidity, conformance to the contour of the body, varying geometric size form factors, varying shape form factors, comfort, resistance to body fluids, resistance to external fluids, temperature stability, corrosion resistance, electrical stability and ease of use.

13. The sensor device of claim 1, comprising a hermetically sealed assembly that houses one or more of the substrate, the circuitry, the processor, the transmitter a memory device, storage, a receiver, and a power source.

14. The sensor device of claim 13, wherein the storage includes a battery compartment configured to house a battery, wherein the battery is the power source and is removable and replaceable.

15. The sensor device of claim 13, wherein the assembly is configured to allow selective replacement, reuse, and disposal of the transmitter, the receiver, the memory device, and the power source.

16. The sensor device of claim 1, comprising a patch having a plurality of sides, wherein at least one side includes a conductive adhesive coating, wherein a first side of the patch is affixed to the bottom of the substrate and the reverse side of the patch is affixed to the body.

17. The sensor device of claim 16, wherein the patch includes perforations configured for one or more of air flow, fluid flow, and comfort.

18. The sensor device of claim 16, wherein the patch is configured to conform to the substrate.

19. The sensor device of claim 16, wherein the patch is configured to be disposable.

20. The sensor device of claim 16, wherein the conductive adhesive coating includes at least one property, wherein the at least one property includes electrical conductivity.

21. The sensor device of claim 1, comprising an adhesive connected to the substrate, wherein the adhesive is directly applied to the substrate for affixing the substrate directly to the body.

22. The sensor device of claim 1, wherein the biological parameters are received from one or more implanted devices implanted in the body.

23. The sensor device of claim 1, wherein the biological parameters are received as a component of an analog electrical signal from the body.

24. The sensor device of claim 1, wherein the processing includes converting the analog signal to a digital signal.

25. The sensor device of claim 1, wherein the transmitter includes one or more of a wireless transmitter and/or a wired transmitter.

26. The sensor device of claim 1, wherein the transmitter uses one or more channels to transmit.

27. The sensor device of claim 1, comprising at least one other transmitter, wherein the at least one other transmitter is configured for transmitting on one or more channels.

28. The sensor device of claim 1, comprising a receiver coupled to the processor, wherein the receiver uses one or more channels to receive.

29. The sensor device of claim 1, comprising a plurality of receivers at least one of which is coupled to the processor, wherein the plurality of receivers each receive on one or more channels.

30. The sensor device of claim 1, comprising at least one other processor, the processors configured for processing one or more types of information.

31. The sensor device of claim 1, comprising a memory device, the memory device storing one or more of the biological parameters and the processed information.

32. The sensor device of claim 1, comprising a second receiver, wherein the second receiver includes one or more of a wired receiver and a wireless receiver.

33. The sensor device of claim 1, wherein the substrate includes a conductive adhesive for the attaching, wherein the conductive adhesive is removable.

34. The sensor device of claim 1, wherein the substrate includes a conductive adhesive formulated for one more of the attaching and timed release of one or more therapeutic drugs.

35. The sensor device of claim 1, wherein the substrate includes a conductive adhesive formulated for one or more of the attaching and timed release of one or more therapeutic drugs.

36. The sensor device of claim 1, wherein the substrate includes a conductive adhesive that is moisture resistant to enable usage in high-moisture environments.

37. The sensor device of claim 1, wherein one or more of the circuitry, the processor, and the transmitter is configured to be programmable.

38. The sensor device of claim 37, wherein programmable includes programmable relative to one or more of time, identification information, user profile information, functionality information, and health information.

39. The sensor device of claim 37, wherein the processor is configured for programming via inputs made at a remote device selected from a group consisting of a cellular telephone and a mobile device carried by the user.

40. The sensor device of claim 37, wherein one of more of the circuitry, the processor, and the transmitter is configured for programming such that the device is reconfigured from a first function to a second function.

41. A system having a sensor device, comprising:
a substrate having conductive adhesive material for communicating electrical signals and attaching to it body of it user;
circuitry coupled to the substrate and operating to acquire electrical signals representing one or more biological parameters of the body and converting the acquired electrical signals from analog to digital format for further processing by a processor;
the processor coupled to the circuitry and the substrate, the processor being programmed to generate processed information by processing the electrical signals representing; the biological parameters including electrical signals received from a heart of the user;

an antenna coupled to the circuitry;

a memory having a database coupled to the processor and carried on the body, the database storing one or more of the electrical signals, the processed information and health information of the user, the health information selected from the group consisting of gastronomic information, dietary information, physical activity information, exercise information, allergy information, information of ingested food, information of ingested medication, user profile, and emergency response information;

a transmitter coupled to the processor and transmitting the electrical signals and the processed information representing the biological parameters, wherein the transmitter uses one or more of wired and/or wireless transmission;

a power source coupled to the substrate and controlled by the processor to deliver calibrated energy to the body in response to the processed information representing one or more biological parameters, such that the energy has a level and intensity sufficient for application through a surface of the body and which is selected by the processor in response to the information sufficient to stimulate a selected heart activity, and where the processor is further programmed to correlate the electrical signals from the heart and render an electrocardiogram representative of the electrical signals;

an identification component communicatively coupled to the processor, wherein the identification component authenticates the communication between the processor and an external device using one or more of individual profile information, individual health information, biometric information of a user and/or identification information of the external device; and, a cellular telephone in wireless communication with the transmitter, the cellular telephone having a local processor programmed to initiate a selected query or action with the processor coupled to the circuitry such that the cellular telephone enables control of the circuitry and further having a display programmed to display a response to the query or action from the processor coupled to the circuitry.

42. A system having a sensor device, comprising:

a substrate having conductive adhesive material for communicating electrical signals and attaching to a body of a user;

circuitry coupled to the substrate and operating; to acquire electrical signals representing one or more biological parameters of the body and converting the acquired electrical signals from analog to digital format for further processing by a processor;

the processor coupled to the circuitry and the substrate, the processor being programmed to generate processed information by processing the electrical signals representing the biological parameters including electrical signals received from a heart of the user, the processor encrypting communications to an external device external to the processor and decrypting communications from the external device;

an antenna coupled to the circuitry;

a memory having a database coupled to the processor and carried on the body, the database storing one or more of the electrical signals, the processed information and health information of the user, the health information selected from the group consisting of gastronomic information, dietary information, physical activity information, exercise information, allergy information, information of ingested food, information of ingested medication, user profile, and emergency response information;

a transmitter coupled to the processor and transmitting the electrical signals and the processed information representing the biological parameters, wherein the transmitter uses one or more of wired and/or wireless transmission;

a power source coupled to the substrate and controlled by the processor to deliver calibrated energy to the body in response to the processed information representing one or more biological parameters, such that the energy has a level and intensity sufficient for application through a surface of the body and which is selected by the processor in response to the information sufficient to stimulate a selected heart activity, and where the processor is further programmed to correlate the electrical signals from the heart and render an electrocardiogram representative of the electrical signals;

an identification component communicatively coupled to the process, wherein the identification component authenticates the communication between the processor and the external device using one or more of individual profile information, individual health information, biometric information of a user and/or identification information of the external device; and, a cellular telephone in wireless communication with the transmitter, the cellular telephone having a local processor programmed to initiate a selected query or action with the processor coupled to the circuitry such that the cellular telephone enables control of the circuitry and further having a display programmed to display a response to the query or action from the processor coupled to the circuitry.

43. A system having a sensor device, comprising:

a substrate having conductive adhesive material or communicating electrical signals and attaching to a body of a user;

circuitry coupled to the substrate and operating to acquire electrical signals representing one or more biological parameters of the body and converting the acquired electrical signals from analog to digital format for further processing by a processor;

the processor coupled to the circuitry and the substrate, the processor being programmed to generate processed information by processing the electrical signals representing the biological parameters including electrical signals received from a heart of the user;

an antenna coupled to the circuitry;

a memory having a database coupled to the processor and carried on the body, the database storing the one or more of the acquired analog electrical signals, the digital electrical signals, the processed information, individual profile information and/or individual health information;

a multi-channel transmitter/receiver coupled to the processor and transmitting and receiving the electrical signals and the processed information representing the biological parameters using one or more of wired and/or wireless communications, the wireless communications using one or more channel of the multi-channel transmitter/receiver and one or more communication protocol selected from the group consisting of cellular communication, Wi-Fi communication, and IP communication;

a power source coupled to the substrate and controlled by the processor to deliver calibrated energy to the body in response to the processed information representing one or more biological parameters, such that the energy has a level and intensity sufficient for application through a surface of the body and which is selected by the processor in response to the information sufficient to stimulate a selected heart activity, and where the processor is further programmed to correlate the electrical signals from the heart and render an electrocardiogram representative of the electrical signals;

an identification component communicatively coupled to the processor, wherein the identification component authenticates the communication between the processor and an external device using one or more of individual profile information, individual health information, biometric information of a user and/or identification information of the device; and, a cellular telephone in wireless communication with the transmitter, the cellular telephone having a local processor programmed to initiate a selected query or action with the processor coupled to the circuitry such that the cellular telephone enables control of the circuitry and further having a display programmed to display a response to the query or action from the processor coupled to the circuitry.

44. A system having a sensor device, comprising:

a substrate having conductive adhesive material for communicating electrical signals and attaching to a body of a user;

circuitry coupled to the substrate and operating to acquire electrical signals representing one or more biological parameters of the body and converting the acquired electrical signals from analog to digital format for further processing by a processor;

the processor coupled to the circuitry and the substrate, the processor being programmed to generate processed information by processing the electrical signals representing the biological parameters including electrical signals received from a heart of the user;

an antenna coupled to the circuitry;

a memory having a database coupled to the processor and carried on the body, the database storing the one or more of the electrical signals, the processed information and health information of the user, the health information selected from the group consisting of gastronomic information, dietary information, physical activity information, exercise information, allergy information, information of ingested food, information of ingested medication, user profile, and emergency response information;

a power source coupled to the substrate and controlled by the processor to deliver calibrated energy to the body in response to the processed information representing one or more biological parameters, such that the energy has a level and intensity sufficient for application through a surface of the body and which is selected by the processor in response to the information sufficient to stimulate a selected heart activity, and where the processor is further programmed to correlate the electrical signals from the heart, and render an electrocardiogram representative of the electrical signals;

an identification component communicatively coupled to the processor, wherein the identification component authenticates the communication between the processor and an external device using one or more of individual profile information, individual health information, biometric information of a user and/or identification information of the device; and, a cellular telephone in wireless communication with the transmitter, the cellular telephone having a local processor programmed to initiate a selected query or action with the processor coupled to the circuitry such that the cellular telephone enables control of the circuitry and further having a display programmed to display a response to the query or action from the processor coupled to the circuitry.

45. The sensor device of claim 44, wherein the processor controls the delivering of calibrated energy by controlling a level of the energy and a duration of the delivering.

46. The sensor device of claim 44, wherein the processor controls the delivering in response to detected undesirable heart activity represented by the biological parameters.

47. The sensor device of claim 44, wherein the processor controls the delivering in response to detected real time electrocardiogram data represented by the biological parameters.

48. The sensor device of claim 44, wherein the processor controls the delivering in response to profile information of the user.

49. The sensor device of claim 44, wherein the processor controls the delivering in response to data of the processed biological information.

50. The sensor device of claim 44, wherein the calibrated energy is a defibrillation pulse that delivers electrical energy to the human heart in order to resynchronize the heart function.

* * * * *